(12) United States Patent
Iizuka et al.

(10) Patent No.: US 8,578,580 B2
(45) Date of Patent: Nov. 12, 2013

(54) QUALITY CONTROL METHOD AND MANUFACTURING METHOD FOR PIPE

(75) Inventors: Yukinori Iizuka, Kawasaki (JP);
Kazuhito Kenmochi, Chiba (JP);
Hiroyasu Yokoyama, Handa (JP);
Tomohiro Inoue, Kawasaki (JP);
Shigeto Sakashita, Kawasaki (JP)

(73) Assignee: JFE Steel Corporation, Tokyo (JP)

( * ) Notice: Subject to any disclaimer, the term of this patent is extended or adjusted under 35 U.S.C. 154(b) by 1011 days.

(21) Appl. No.: 12/449,746

(22) PCT Filed: May 18, 2007

(86) PCT No.: PCT/JP2007/060663
§ 371 (c)(1),
(2), (4) Date: Nov. 20, 2009

(87) PCT Pub. No.: WO2008/105112
PCT Pub. Date: Sep. 4, 2008

(65) Prior Publication Data
US 2010/0064495 A1   Mar. 18, 2010

(30) Foreign Application Priority Data
Feb. 28, 2007   (JP) ................. 2007-048810

(51) Int. Cl.
*B23Q 17/20* (2006.01)
*G01N 29/04* (2006.01)

(52) U.S. Cl.
USPC ............ 29/407.01; 29/407.04; 29/407.05; 73/588; 73/622

(58) Field of Classification Search
USPC ............ 29/407.01, 407.04, 407.05, 407.07; 73/588, 622
See application file for complete search history.

(56) References Cited

U.S. PATENT DOCUMENTS

| 3,683,680 A | * | 8/1972 | Johnson et al. ........... 73/628 |
| 4,699,007 A | * | 10/1987 | Kawashima et al. ....... 73/622 |
| 5,431,054 A | * | 7/1995 | Reeves et al. ............. 73/612 |
| 2006/0090319 A1 | * | 5/2006 | Howe ..................... 29/407.05 |

FOREIGN PATENT DOCUMENTS

| JP | A-60-20536 | 2/1985 |
| JP | A-61-111461 | 5/1986 |
| JP | A-4-274756 | 9/1992 |
| JP | A-7-35729 | 2/1995 |
| JP | A-11-183446 | 7/1999 |
| JP | B2-3165888 | 3/2001 |
| JP | B2-3721827 | 9/2005 |
| JP | B2-3731369 | 10/2005 |
| JP | A-2007-874 | 1/2007 |
| JP | A-2007-163470 | 6/2007 |

OTHER PUBLICATIONS

International Search Report for International Application No. PCT/JP2007/060663, issued Aug. 7, 2007.

* cited by examiner

*Primary Examiner* — Jermie Cozart
(74) *Attorney, Agent, or Firm* — Oliff & Berridge, PLC

(57) ABSTRACT

According to the present invention, penetrators can be adequately determined as flaws. In particular, a welded zone of a pipe is subjected to ultrasonic flaw detection at least in a pipe axial direction, and the quality of the pipe is evaluated using observed values in units of a predetermined area in a pipe thickness direction and the pipe axial direction. The length of one side of the predetermined area is an ultrasound beam width or more and a pipe thickness or less. The quality of the pipe can be evaluated while shifting the predetermined area in the pipe axial direction by using an average value of the observed values within the predetermined area. The length of one side of the predetermined area can be made an ultrasound beam width or more and a pipe thickness or less.

14 Claims, 27 Drawing Sheets

MECHANICAL PROPERTY VALUES OF EVALUATION SAMPLE

50 MHz C-SCAN RESULTS AT 100 μm BEAM DIAMETER
FIG. 4A  C-SCAN DATA OF SAMPLE A
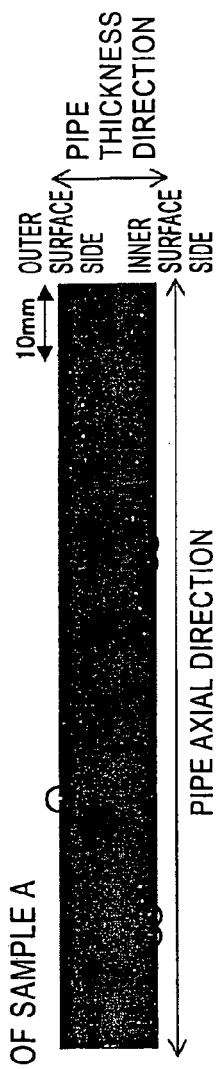
FIG. 4B  SIGNAL STRENGTH DISTRIBUTION OF SAMPLE A
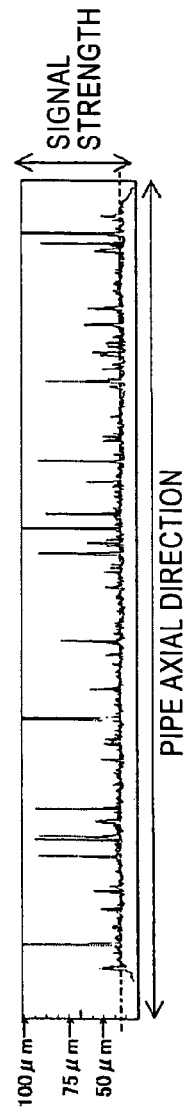
FIG. 4C  C-SCAN DATA OF SAMPLE B
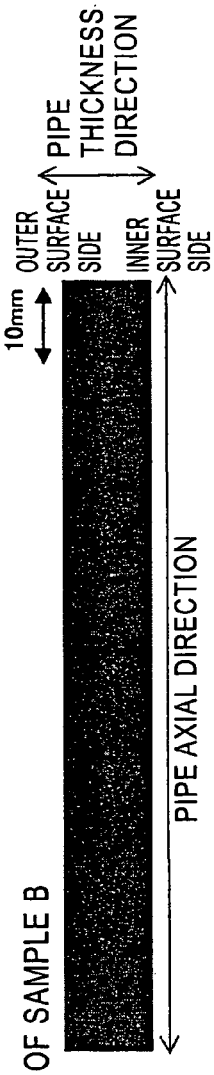
FIG. 4D  SIGNAL STRENGTH DISTRIBUTION OF SAMPLE B
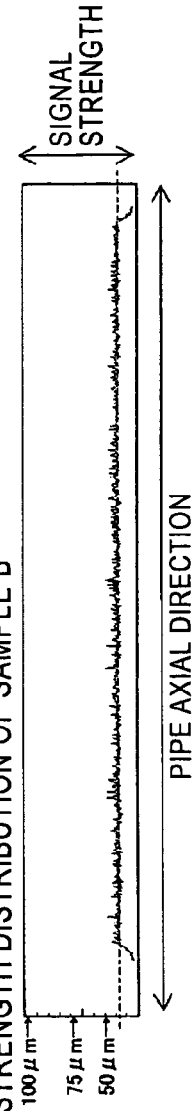

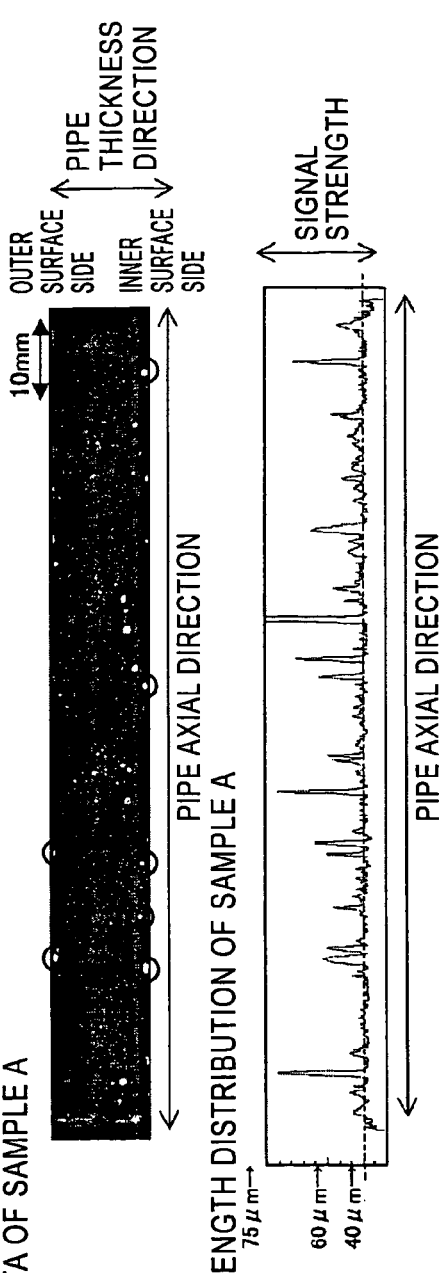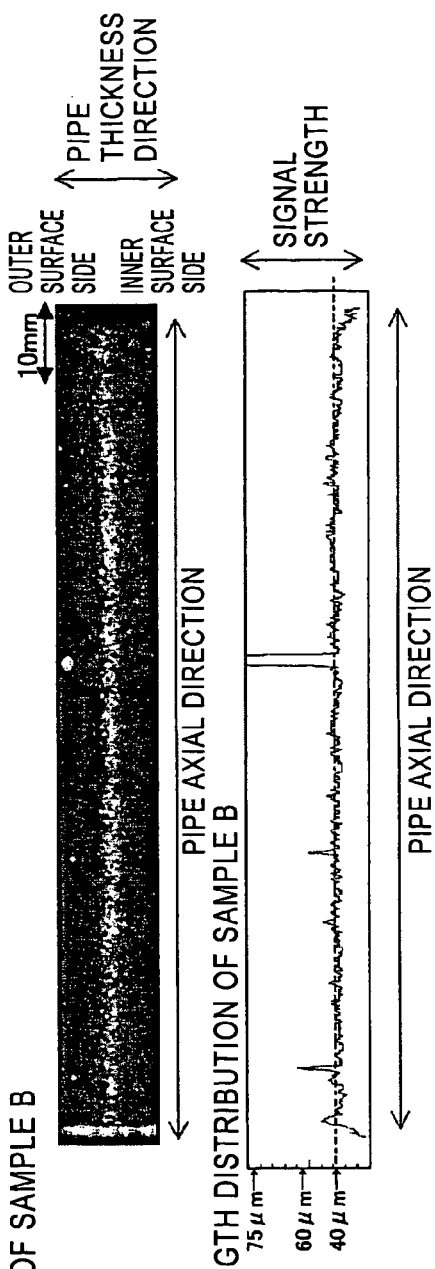
FIG. 5A  C-SCAN DATA OF SAMPLE A
FIG. 5B  SIGNAL STRENGTH DISTRIBUTION OF SAMPLE A
FIG. 5C  C-SCAN DATA OF SAMPLE B
FIG. 5D  SIGNAL STRENGTH DISTRIBUTION OF SAMPLE B

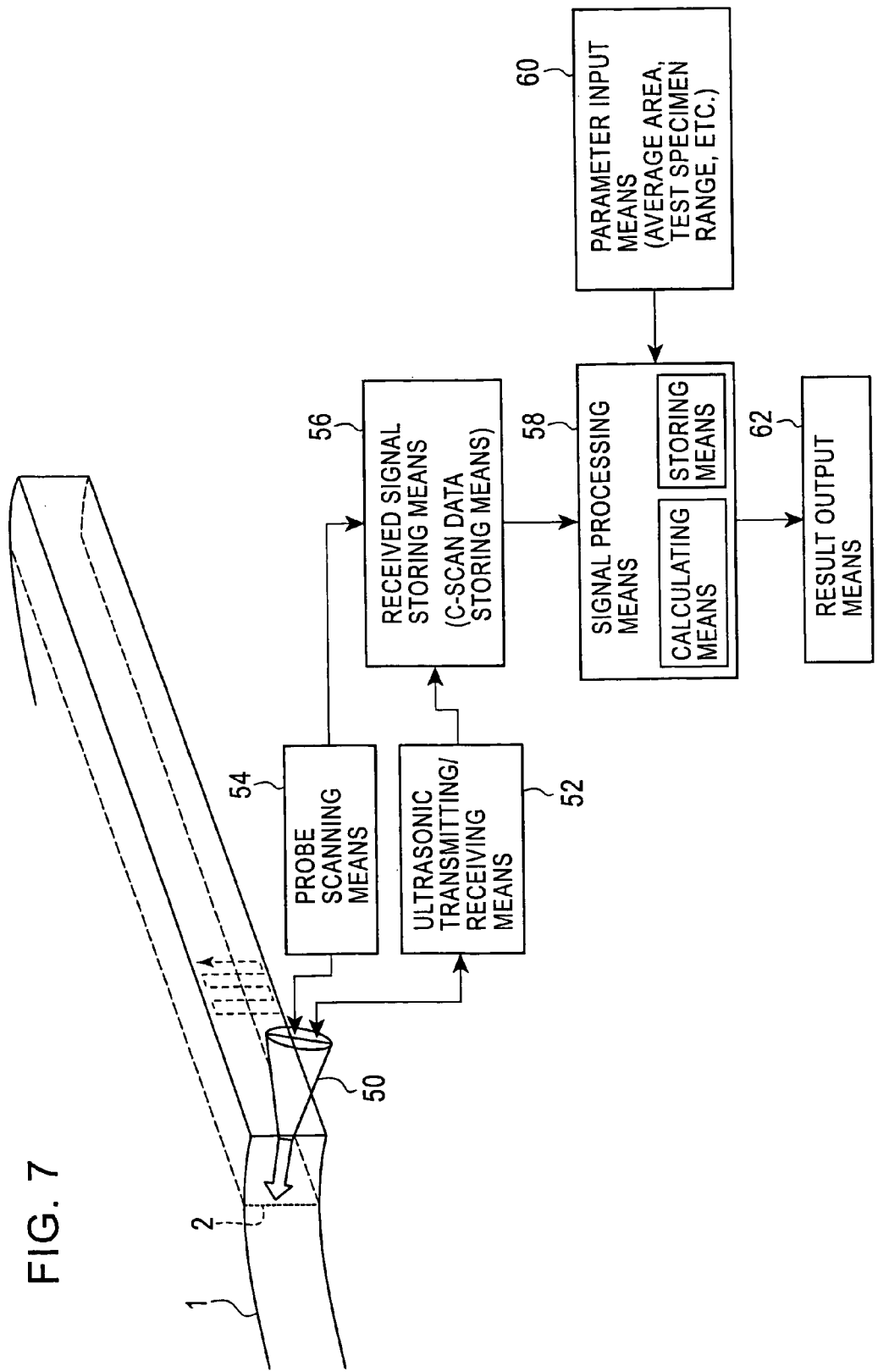

STEP 1: START SCANNING, FOCAL POSITION AT INNER SURFACE SIDE

STEP 2: SCAN WHILE SHIFTING FOCAL POSITION TOWARD OUTER SURFACE SIDE

STEP 3: SCAN WHILE SHIFTING FOCAL POSITION TOWARD OUTER SURFACE SIDE

STEP 4: END SCANNING, FOCAL POSITION AT OUTER SURFACE SIDE

FAIL/PASS  FAIL/PASS

FAIL/PASS  FAIL/PASS

| SCANNING LINE | TRANSDUCER No. | NUMBER OF TRANSDUCERS | DEFLECTION ANGLE | FOCAL LENGTH |
|---|---|---|---|---|
| A | 17-22 | 6 | -6.0° | 31.7 mm |
| B | 71-90 | 20 | 0 | 103 mm |
| C | 124-155 | 32 | -6.0° | 177 mm |

QUALITY CONTROL METHOD AND MANUFACTURING METHOD FOR PIPE

TECHNICAL FIELD

The present invention relates to a quality control method and a manufacturing method for a pipe by which minute flaws occurring in welded zones of welded steel pipes are accurately detected by ultrasonic flaw detection.

BACKGROUND ART

Quality of welded zones is of crucial importance for welded steel pipes, and, in manufacturing processes, on-line flaw detection is generally conducted on welded zones through ultrasonic angle-beam flaw detection. This technique involves causing an ultrasonic wave to be obliquely incident on the surface of the work to be inspected and detecting inner/outer surface defects and subsurface defects of the work on the basis of the reflected waves from the defects. Typically, for example, a reflection method using an ultrasound beam having a 45° refractive angle at 5 MHz is applied to electric resistance welded steel pipes to detect millimeter-order defects, e.g., poor penetration, burn-through, and cracks caused by inclusions.

Recently, the quality requirements for welded steel pipes have become stringent, and detection of flaws smaller than those conventionally detected is required. Examples thereof are cold junction flaws and minute penetrators in electric resistance welded steel pipes and blowholes in laser welded pipes. These flaws range from several tens to several hundred micrometers in size, which are extremely small. These flaws can occur at any locations along a weld line from the inner surface to the outer surface, and the point incidence of the ultrasound beam may differ from its point of return depending on the positions of the flaws. Due to these factors, conventionally practiced ultrasonic flaw detection techniques frequently fail to detect such flaws, and a more accurate flaw detection technique that can be used in quality control of steel pipe welded zones has been desired.

The following related arts have been disclosed as a method for detecting minute flaws for use in quality control of welded steel pipes. Japanese Unexamined Patent Application Publication No. 60-205356 describes use of a point focus-type probe having a frequency of 8 MHz or higher in angle beam testing to improve the detectability for penetrators. Japanese Unexamined Patent Application Publication No. 11-183446 describes detection of blowholes by sector-scanning a welded zone from the inner surface side to the outer surface side with an array probe that forms a focus beam to improve the detectability.

Japanese Unexamined Patent Application Publication No. 61-111461 describes detection of cold joint flaws, which are mixed minute FeO grains several micrometers or smaller in size taking form of clusters, by causing an ultrasonic wave having a frequency of 25 MHz to 500 MHz to be incident on the welded zone from the pipe outer surface-side at an angle of incidence of 0° to 20°. Japanese Unexamined Patent Application Publication No. 7-35729 describes use of a plurality of 20-80 MHz point focus-type probes arranged so that their focusing positions are arranged at a pitch of 3 mm or less from directly above the seam to detect blowholes 0.1 mm or more in size.

It should be noted here that in the Disclosure of the Invention, Japanese Unexamined Patent Application Publication No. 4-274756 and "Ultrasonic Flaw Detection Series (II)—Ultrasonic flaw detection of welded steel pipes" edited by the Iron and Steel Institute of Japan, 1988, pp. 28-31 are cited.

However, the disclosed techniques described above still have the following problems. First, for the technique disclosed in Japanese Unexamined Patent Application Publication No. 60-205356, since the beam width of the focused ultrasonic wave is small, a large number of channels are needed to completely detect flaws in all parts of the welded zone in the depth direction (thickness direction of the steel pipes) and this increases the equipment cost. Moreover, the centering control or the like required in the event of pipe size change is very cumbersome. Furthermore, when the flaw shape is not blowhole-like but is planar such as in the case of penetrators and cold junctions and when such a flaw is located inside the wall, the reflected wave travels in a direction different from the direction of incidence and this renders it difficult to detect such a flaw.

According to the technique disclosed in Japanese Unexamined Patent Application Publication No. 11-183446, only one array probe is needed and the setting required in the event of size change can be conducted electronically. Thus, although this technique does not face the first problem of Japanese Unexamined. Patent Application Publication No. 60-205356 but the second problem remains unresolved.

When the flaw shape is planar as described above, for example in the case of electric resistance welded steel pipes, the seam zone is upset and thus the width of the flaw as viewed from directly above the seam is as small as 100 µm or less. Thus, even with the techniques described in Japanese Unexamined Patent. Application Publication No. 61-111461 and Japanese Unexamined Patent Application Publication No. 7-35729, the reflected waves from the flaws are actually very weak and difficult to detect in many cases. Moreover, since about 1 to 2 mm of the portion near the surface echo forms a dead zone due to reverberation of the surface echo, there is another problem that flaws located near the outer surface cannot be detected.

As discussed above, according to the techniques for detecting minute flaws about several hundred micrometers or smaller in size that occur in the welded zones of the welded pipes in the pipe axial direction, the detection performance is not sufficient and these techniques have difficulty meeting the stringent quality control requirements of recent years. Development of technology that resolves these problems has been desired.

The present invention has been made under the above-described circumstances and aims to assuredly conduct quality control of electric resistance welded steel pipes that require stringent quality control.

DISCLOSURE OF INVENTION

To overcome the problems described above, the following specific measures are provided.

In the embodiments, the present invention provides a quality control method for a pipe, comprising subjecting a welded zone of a pipe to ultrasonic flaw detection at least in a pipe axial direction, and evaluating a quality of the pipe using observed values in units of a predetermined area in a pipe thickness direction and the pipe axial direction.

The present invention further provides the quality control method as set forth above, wherein a length of one side of the predetermined area may be an ultrasound beam width or more and a pipe thickness or less.

The present invention further provides the quality control method as set forth above, wherein the quality of the pipe may be evaluated while shifting the predetermined area in the pipe axial direction.

The present invention further provides the quality control method as set forth above, wherein the quality of the pipe may be evaluated while shifting the predetermined area in the pipe thickness direction.

The present invention further provides the quality control method as set forth above, wherein the quality of the pipe may be evaluated using an average value of the observed values within the predetermined area.

The present invention further provides the quality control method as set forth above, wherein among the predetermined areas in the pipe thickness direction, a maximum average value at the same position in the pipe axial direction may be determined and the quality of the pipe may be evaluated using the maximum average value.

The present invention further provides the quality control method as set forth above, wherein among predetermined areas in the pipe thickness direction, a maximum average value in a particular pipe-thickness-direction range at the same position in the pipe axial direction may be determined and the quality of the pipe may be evaluated using the maximum average value.

The present invention further provides the quality control method as set forth above, wherein the maximum average value at each position in the pipe axial direction may be plotted into a chart.

The present invention further provides the quality control method as set forth above, wherein the ultrasonic flaw detection may be conducted with an ultrasonic flaw detector comprising a transmission unit configured to transmit an ultrasound to a welded surface of a welded zone of the pipe, the welded zone extending in the pipe axial direction, and a reception unit configured to receive part or all of a reflected wave from the welded surface, wherein the transmission unit and the reception unit include transmission/reception units which are separate transducer groups on one or more array probes arranged in a pipe circumferential direction.

The present invention further provides the quality control method as set forth above, wherein the transmission unit may transmit an ultrasound so that the ultrasound is incident on the welded surface of the welded zone of the pipe, the welded zone extending in the pipe axial direction, and on an inner surface of the pipe respectively at an angle in the range of 33.2° to 56.8°, and the reception unit may be configured to receive part or all of the reflected wave reflected in a direction within the range of −12° to 16° with respect to a mirror reflection direction at the welded surface.

The present invention further provides the quality control method as set forth above, wherein a beam width of the ultrasound is in the range of 0.5 mm to 2.5 mm at the welded surface.

The present invention further provides a manufacturing method for a pipe, comprising a manufacturing step of manufacturing a pipe; and a quality control step of controlling the quality by employing the quality control method as set forth above.

It should be noted that the focusing position of the transmission beam and the focusing position of the reception beam are each not necessarily one particular point but a regional range corresponding to the beam width at the position where the transmission beam or the reception beam is focused, and each have a beam width in a cross-section of the pipe and in the pipe axial direction orthogonal to the cross section. The values thereof are determined by the materials and the ultrasonic data.

According to the present invention, flaws such as penetrators can be adequately determined and detected. Thus, the welding process can be improved to avoid occurrence of minute flaws that affect the mechanical properties of welded zones of welded steel pipes and quality control that can screen the products to prevent flawed products can be achieved. Thus, the quality of the welded steel pipes can be drastically improved and the welded steel pipes can be used in operation conditions more stringent than conventionally practiced.

BRIEF DESCRIPTION OF DRAWINGS

FIGS. 4A to 4D are diagrams also showing the C-scan results at 50 MHz and a beam width of 100 μm.

FIGS. 5A to 5D are diagrams also showing the C-scan results at 50 MHz and a beam width of 250 μm.

FIG. 7 is a diagram showing a functional structure example for a comparative experiment of C-scan and Charpy impact test.

REFERENCE NUMERALS

1: steel pipe, 2: welded zone, 3: flaw, 4: water, 5: linear array probe, 6: transmitter transducer group, 7: receiver transducer group, 8: transmission beam, 9: reception beam, 10: flaw inspection condition calculating unit, 11: delay time setting unit, 12: pulser, 13: transducer in the linear array probe, 14: reception amplifier, 15: delay time setting unit, 16: integration processing unit, 17: gate evaluation unit, 30: work size input unit, 31: array probe memory unit, 32: aperture width controlling unit, 33: gate position memory unit, 34: array transmission rule memory unit, 35: array reception rule memory unit, 36: array transmission unit, 37: array reception unit, 38: gate unit, 39: detection threshold input unit, 40: flaw determining unit Embodiments for Carrying Out the Invention The inventors of the present invention have conducted extensive researches and made a novel, useful discovery that the presence of flaws such as penetrators remaining in the welded zones is affecting the mechanical properties of the welded surfaces of electric resistance welded steel pipes in the pipe axial direction, and that although the size of one flaw alone is negligibly small, the amount of flaws (the number of flaws found in a predetermined area) significantly affects the mechanical properties of the welded zones.

Initially, the inventors have thought that it is the size of the penetrators that significantly affects the mechanical properties of the welded zones of the electric resistance welded steel pipes, and that the mechanical properties will be enhanced if the size of the penetrators present in the welded zones is reduced to a certain extent. As a result of search for the flaw detection method that can detect such flaws, the inventors have conceived a flaw detection technique in which the ultrasonic beam width for transmission and reception is small in comparison with the conventional ultrasonic flaw detection techniques. However, when this ultrasonic flaw detection technique using a smaller beam width was employed to evaluate the presence of penetrators and the results were compared with mechanical properties, the outcome was completely unexpected. In other words, there were cases in which mechanical properties were good despite detection of penetrators and cases in which mechanical properties were poor despite nondetection of penetrators. The inventors have conducted further detailed investigations and arrived at a very useful finding not known before, i.e., the mechanical properties are correlated with penetrators that take form of minute flaws several micrometers in size scattered over a wide region. On the basis of this finding, an ultrasonic flaw detection technique was developed to detect such flaws.

Figure 1:
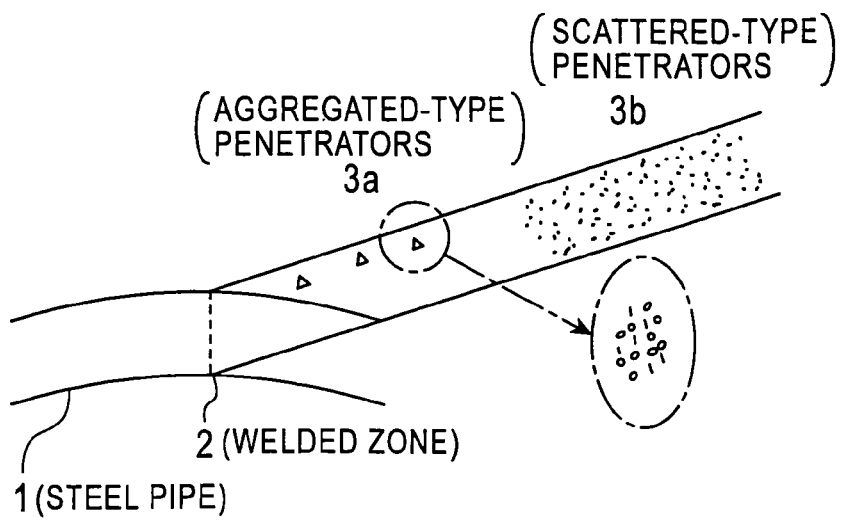
FIG. 1 is a perspective view showing types of minute penetrators identified by investigations conducted by the inventor.

The form of penetrators will now be described with reference to FIG. 1. Initially, the minute flaws such as penetrators that affect the mechanical properties were thought to be the oxides (mainly of the Si—Mn system) several micrometers in size gathered closely (aggregated) in a region several tens to several hundred micrometers in size, such as 3a in a welded zone 2 of a steel pipe 1, and were thought to appear as one flaw (in this specification, these penetrators are also referred to as "aggregated-type penetrators"). However, the investigations of the inventors have found the presence of penetrators taking a form in which a large number of oxides several micrometers in size are distributed (scattered) over a wide region, as indicated by 3b (in this specification, these penetrators are also referred to as "scattered-type penetrators"). The scattered-type penetrators are not clearly detected by the conventional detection techniques, and their cross-sectional observation is extremely difficult to due to a low density. Thus, their presence was not known before. As a result of the detailed investigations conducted by the inventors, it was discovered that the scattered-type penetrators are an important detection target in evaluating the mechanical properties, in particular, in evaluating the level that exhibits excellent characteristics (the level at which stringent quality control is required). The inventors then conceived, on the basis of this discovery, the invention related to quality control of welded zones of electric resistance welded steel pipes.

Figure 2:
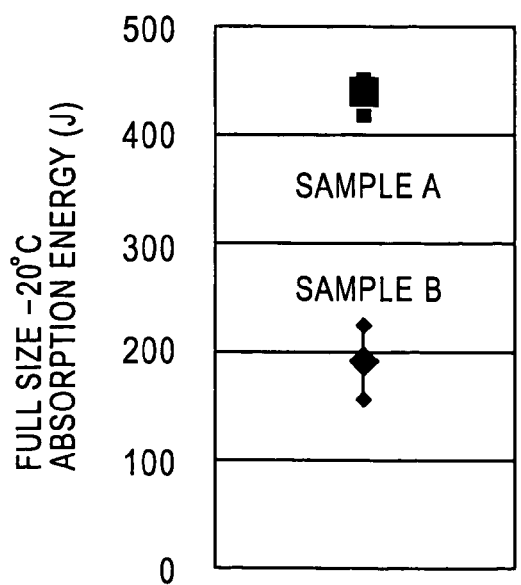
FIG. 2 is a graph showing sample results of Charpy impact test.

FIG. 2 shows the results of the Charpy impact test on Charpy specimens cut out from sample pipes. The results of the Charpy impact test show that Sample A (number of samples =3) has good mechanical property, i.e., an absorption energy of 400 J or higher, and Sample B (number of samples=3) has an absorption energy of about 200 J.

Figure 3:
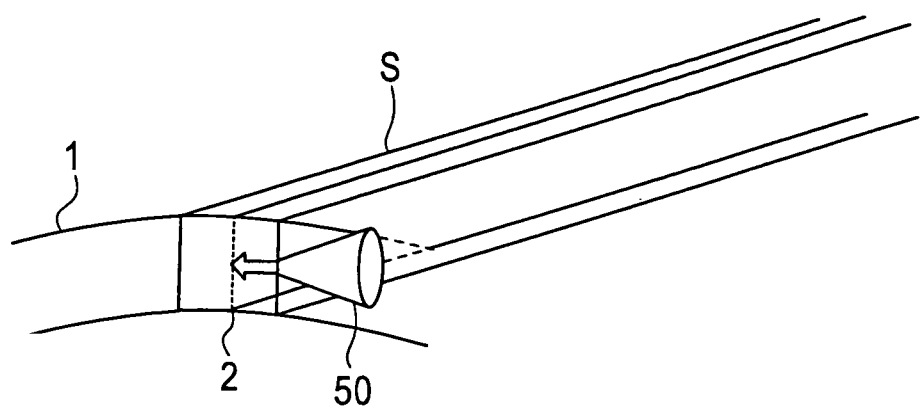
FIG. 3 is a diagram showing a C-scan method conducted on a seam slice material for explaining the principle of the present invention.

In the vicinity of the position where a Charpy specimen was cut out, as shown in FIG. 3, the welded zone 2 of the welded surface of the electric resistance welded pipe 1 in the pipe axial direction was cut out (sliced) at a position 4 mm from the welded surface in the circumferential direction to prepare Sample S. The cut-out surface of Sample S was C-scanned with a focusing-type ultrasonic probe 50 to conduct flaw detection, and the results were compared with the Charpy impact test results. First, the inventors thought that the presence of the aggregated-type penetrators closely gathered in the region several tens to several hundred micrometers in size described above affected the mechanical properties of the welded zone, and thus flaw detection was conducted using a 50 MHz focusing-type ultrasound probe 50 at a reduced beam width of 100 μm to detect such penetrators. The results are shown in FIGS. 4A to 4D. FIG. 4A shows the C-scan data of Sample A, where the horizontal axis indicates the pipe axial direction, the vertical axis indicates the thickness direction, and the signal strength is indicated in shades (lighter color is indicated as the signal strength becomes stronger). FIG. 4B is a graph showing the maximum signal strength in the thickness direction at the same position in the pipe axial direction on the basis of the data shown in FIG. 4A, where the horizontal axis indicates the position in the pipe axial direction and the maximum signal strength is plotted in the vertical axis. Similarly, FIG. 4C and FIG. 4D show the results of ultrasonic flaw detection conducted on Sample B. In the results shown in FIG. 4B and FIG. 4D, values of flaw diameters derived from the maximum signal strengths in the thickness direction are indicated in the vertical axis. In Sample A, many flaw indications (corresponding to the aggregated-type penetrators described above) having a signal strength corresponding to a flaw diameter of 50 μm or more were scattered. In Sample B, such scattered flaw indications were rarely observed. This result shows that the mechanical properties are good despite the presence of aggregated-type penetrators and that the absorption energy is low for samples in which penetrators are rarely detected. This result is completely opposite to what the inventors have initially anticipated.

Next, the inventors changed various measurement conditions and carried out measurement. Among these conditions, when the beam width was increased (in particular, the beam with is increased from 100 μm to 250 μm), it was found that signals which had not been confirmed before could be obtained. The results are shown in FIGS. 5A to 5D. As in FIGS. 4A and 4B, for Sample A in which good mechanical properties were observed in the Charpy impact test, the base signal level was the signal level corresponding to a flaw diameter of about 25 μm, which was significantly smaller than a flaw diameter of 40 μm, and flaw signals with high signal levels corresponding to a flaw diameter of about 100 μm were occasionally observed. In contrast, as in FIGS. 4C and 4D, for Sample B, although no flaw signals of high signal levels were observed, signals indicating the signal strengths corresponding to a flaw diameter of about 40 μm (light-colored indications that appear in the image of the drawing) were observed throughout the entire length in the pipe axial direction. On the basis of these results, the inventors have found that the flaws that have relatively low signal levels, i.e., signal levels corresponding to a flaw diameter of about 40 μm, but are widely distributed affect the mechanical properties of the welded zone significantly.

A cross-section of Sample B was observed with an electron microscope. It was confirmed that minute oxides (minute penetrators) each 5 μm to 20 μm in size were sparsely present at the flaw indication sites observed in Sample B, which supports the results of the C-scan.

Figure 6:
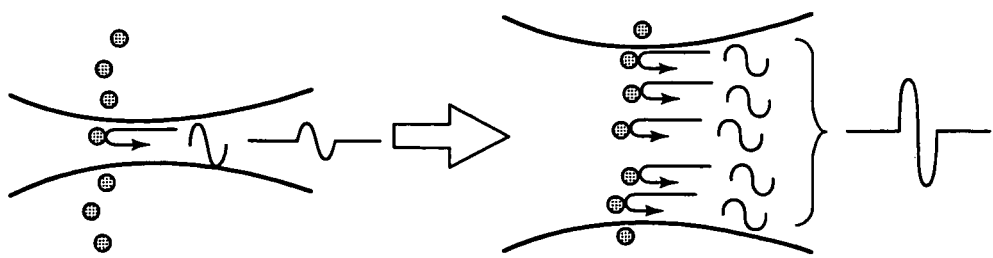
FIG. 6 is a detection image in which reflection sources are scattered.

The reason why increasing the ultrasound beam width resulted in detection of a faint echo band will now be discussed. As shown in FIG. 6, consider a state in which micro reflection sources are homogeneously scattered in a wide area. If the beam width is small, fewer micro reflection sources are included in the beam and the ratio of the total area of the flaws to the area of the beam is small. As a result, the reflection echo becomes weak. In contrast, if the beam width is increased, more micro reflection sources are included in the beam and the ratio of the total area of the flaws to the area of the beam increases. Thus, although the echo from individual micro reflection sources is weak, the echo is accumulated and intensified, resulting in an increase in detection signal level.

On the basis of these results, a new finding was derived in that penetrators each having a significantly small flaw diameter and being distributed over a wide area (scattered-type penetrators) also affect the mechanical properties of the welded zone, that there is a preferable beam width range for highly accurate evaluation, and that the quality control is possible on the basis of the results detected under such conditions.

On the basis of the findings and analysis made by the inventors, it was found that although the beam focusing degree employed in the related art does not achieve sufficient sensitivity for detecting the scattered-type penetrators in the welded zone of an electric resistance welded steel pipe, excessive focusing does not achieve detection, either. The essence of the invention of this application is arrived at by conceiving that there is a preferable range of the ultrasound beam width for detecting penetrators that significantly affect the quality of the welded zone by ultrasonic flaw detection and that the results detected at that beam width can be used to calculate the index values for evaluating the quality of the welded zone of the electric resistance welded steel pipe and quality control can be carried out on the basis of the index value.

In this invention, since an array probe is used, the beam shape is rectangular. Thus, the beam width referred in this specification shall be considered to be an effective value which is a square root of the beam area. However, it is also possible that the focusing in the pipe axial direction is not necessary such as when the penetrators are continuously present in the pipe axial direction. In such a case, the beam width can be considered to be the beam width in the pipe thickness direction.

First, in order to investigate the quality control method of the present invention, flaw detection was conducted under conditions that can detect the scattered-type penetrators, which are minute flaws distributed over a wide region and affect the mechanical properties of the welded zone, by using a C-scan technique, and the results of the flaw detection were comparatively evaluated. One example of the system for evaluation is shown in FIG. 7. The system is constituted by a probe 50 for carrying out ultrasonic flaw detection on a cut-out welded surface by transmitting and receiving ultrasonic waves, ultrasonic transmitting/receiving means 52 for controlling the transmission and reception of the ultrasonic waves at the probe 50, probe scanning means 54 for sequentially scanning the welded surface of the cut-out sample with a probe in the pipe axial direction and the pipe thickness direction to conduct C-scan, received signal storing means 56 for storing the C-scan data, signal processing means 58 for arithmetically processing the C-scan data, parameter input means 60 for inputting parameters necessary for the arithmetic processing, and result output means 62.

The received signal storing means 56 is configured to store the signals received by the ultrasonic probe 50 by associating the received signals with the positions of welded surface scanned by the probe scanning means 54. For example, the received signal storing means 56 is a memory (two-dimension memory) that can store the strengths of the received signals with respect to the pipe axial direction and pipe thickness direction. In other words, it is C-scan data storing means that has a function of storing the C-scan data.

The signal processing means 58 is configured to calculate the index values correlated to mechanical properties with respect to the data of this memory when the parameters required for the arithmetic processing described below are input through the parameter input means 60, and the results are displayed in a screen or printed through result output means such as a CRT, a liquid-crystal monitor, a printer, or the like.

Figure 8:
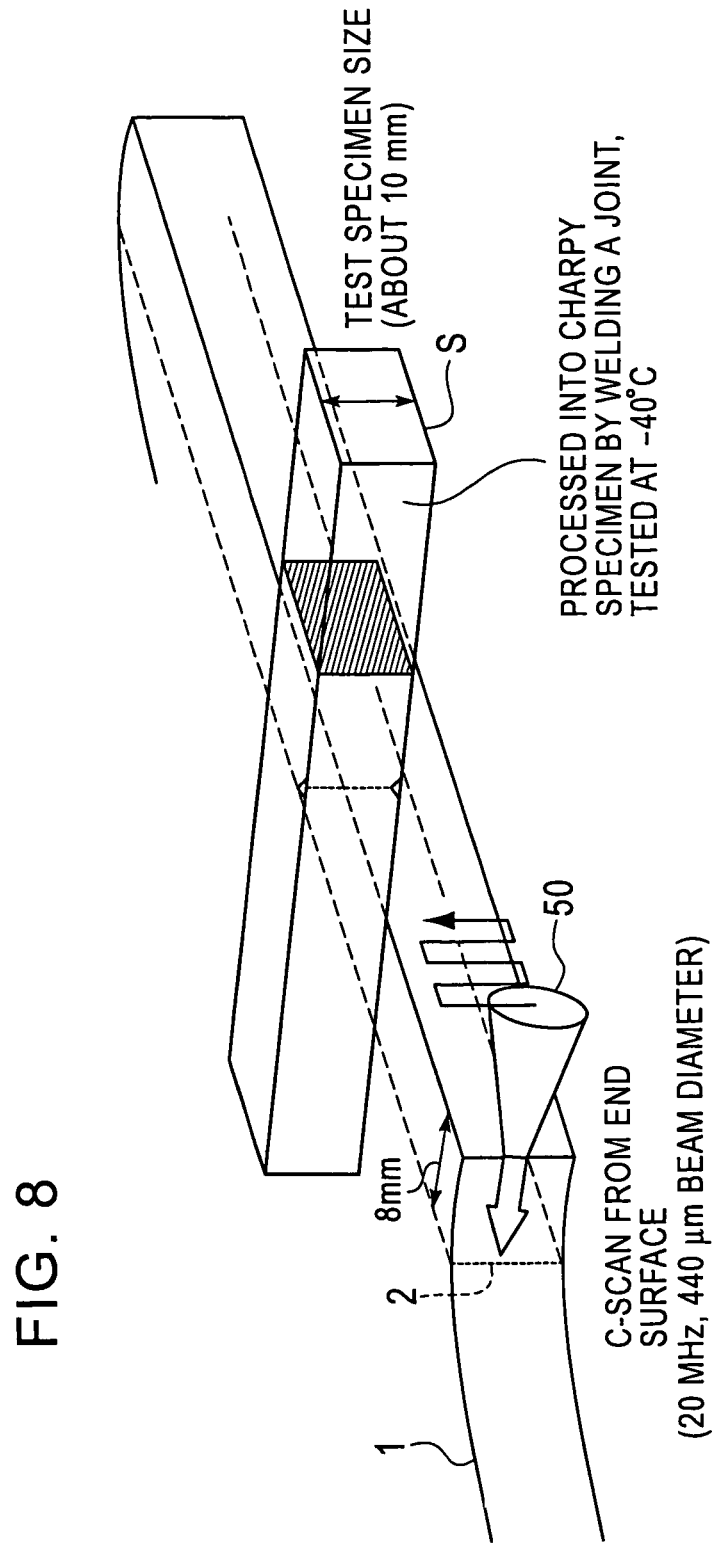
FIG. 8 is a perspective view showing contrast between the C-scan and the Charpy impact test to explain the principle of the present invention.

In particular, as shown in FIG. 8, a sample cut out (sliced) at a position 8 mm from the welded surface (seam) was prepared, and a 20 MHz point focused probe 50 was used from an end surface while controlling the beam width at the welded surface to be 440 μm using this system. The beam width of 440 μm was selected since it was within a preferable range for detecting scattered-type penetrators, i.e., minute flaws distributed over a wide region (e.g., the region may be 1.5 mm×1.5 mm or 2 mm×2 mm), by C-scan. C-scan was conducted on the welded surface in the thickness direction and the pipe axial direction.

Next, the mechanical properties at the same positions where the C-scan was conducted were determined. In particular, a sample 10 mm in the longitudinal direction and about 10 mm in the thickness direction was cut out, a joint was pressure-welded while avoiding a thermal effect on a notch to prepare a Charpy specimen, and Charpy impact test was conducted at −40° C. to measure the Charpy absorption energy at that position.

The values that could be used as the index values to be associated with the mechanical properties were calculated from the measured data detected with an ultrasound (ultrasonic echo height), and whether the correlation can be established between the resulting values and the Charpy absorption energy was evaluated.

Figure 9:
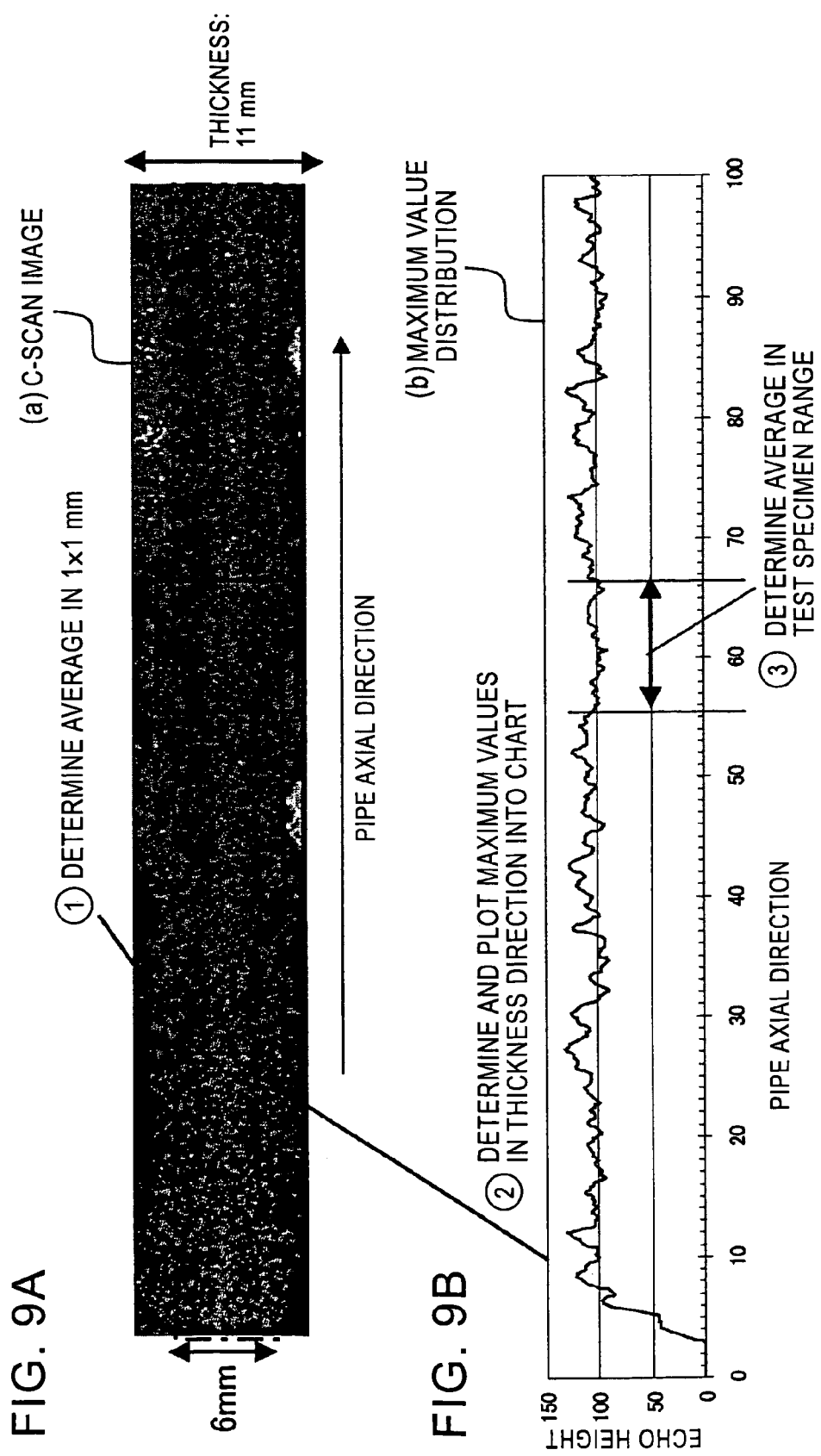
FIGS. 9A and 9B are also diagrams showing C-scan data processing.

FIGS. 9A and 9B show an example of a method for arithmetically processing the index values to be compared with the mechanical properties.

FIG. 9A is an image obtained by C-scan. The vertical axis indicate the thickness direction and the horizontal axis indicates the pipe axial direction. The light-colored shaded portions indicate that the ultrasonic echo is high and the defect density is high. The dark-colored shaded portions indicate that the ultrasonic echo is low and the defect density is low. On the basis of this data, it is found that many minute flaws are distributed in a 6 mm region near the center in the 11 mm-thick wall.

The data was subjected to the following process to obtain the index values.

i) For each data, the average values in particular regions (for example, 1 mm×1 mm regions) are calculated, and the average value data is prepared.

ii) For the average data, maximum value distribution data obtained by determining the maximum values in the thickness direction at the same positions in the pipe axial direction is calculated. The maximum value distribution data corresponds to FIG. 9B.

iii) On the basis of the maximum value distribution data, the average value in the range where the Charpy specimen is cut out is calculated and the calculated value is assumed to be the index to be compared with the Charpy test results.

Note that the process described above was conducted on a 6 mm-region near the center in the thickness direction since the flaw distribution shows concentration near the center of the wall.

Figure 10:
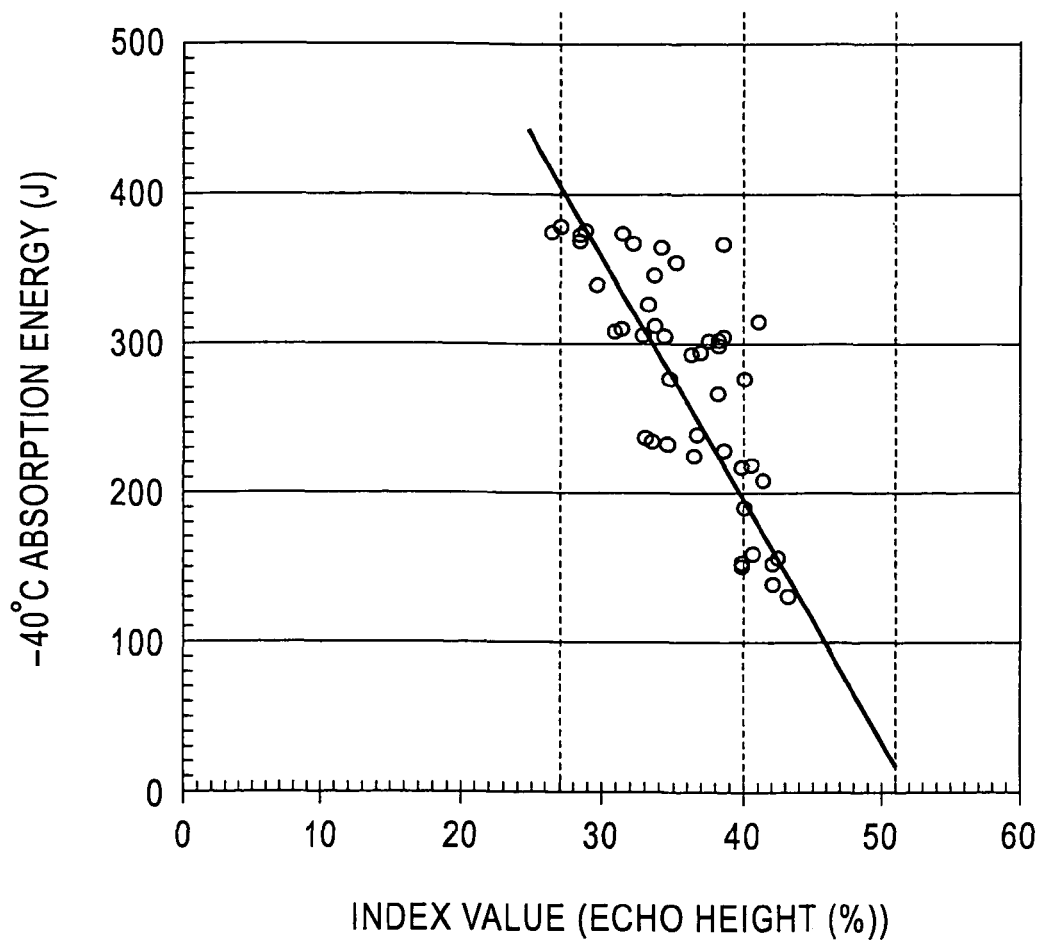
FIG. 10 is a graph comparatively showing the C-scan echo height and the Charpy absorption energy.

These processes are conducted on a plurality of positions of many samples. The relationship between the index values obtained by C-scan and the results of the Charpy test is shown in FIG. 10. FIG. 10 is data in which the horizontal axis indicates the index values and the results of the Charpy test are plotted along the vertical axis.

As obvious from the data, there is a tendency that the smaller the index values, the better the mechanical properties. Thus, it has been found that the quality of the welded zone can be evaluated on the basis of the index value.

Figure 11:
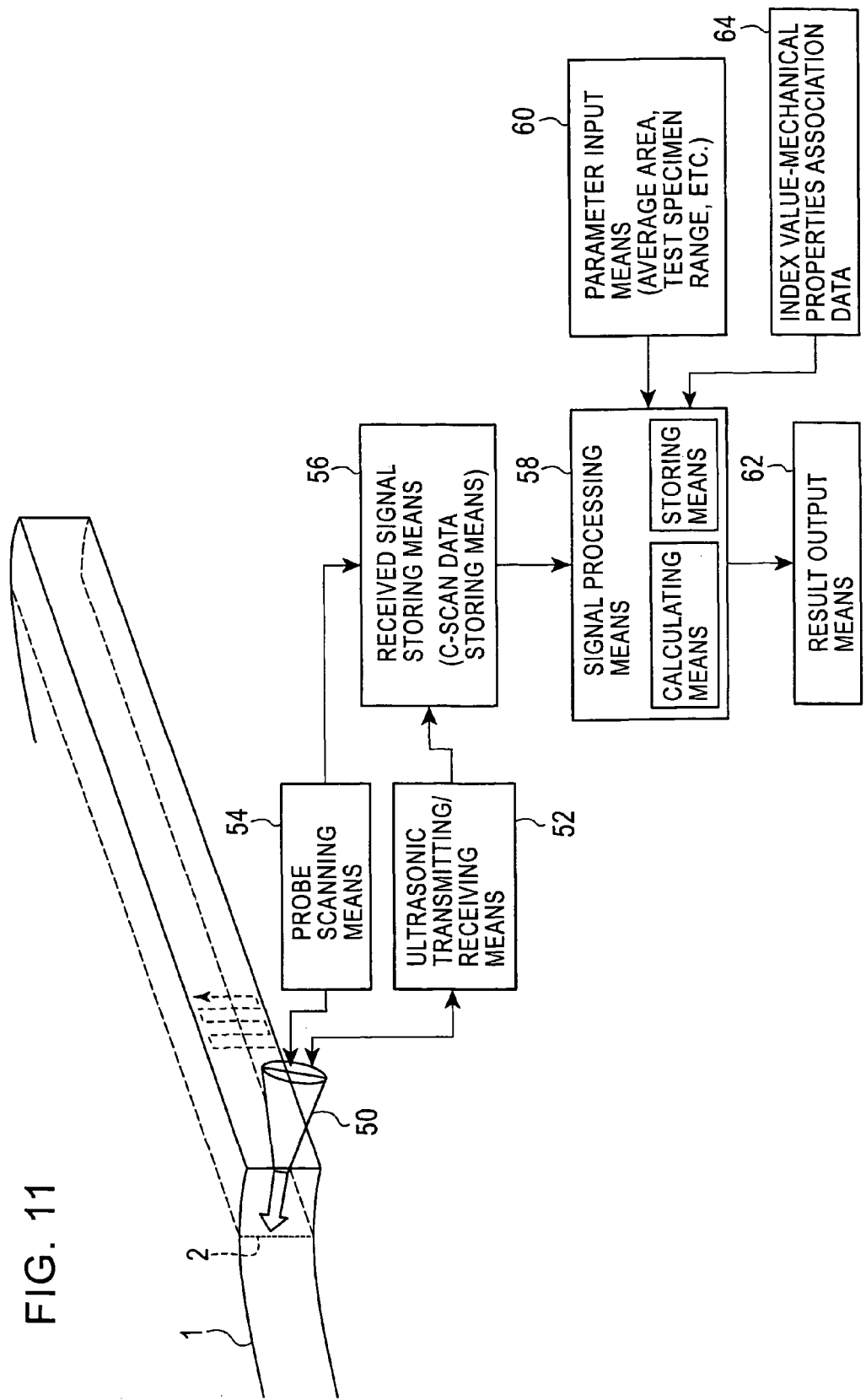
FIG. 11 is a diagram showing a functional structure example for a comparative experiment of C-scan and Charpy impact test.

Accordingly, if the processes of i) to iii) above can be conducted with the signal processing means 58 shown in FIG. 11, the mechanical properties of the welded zone can be evaluated and the quality control becomes possible. Note that the system shown in FIG. 11 is the system shown in FIG. 7 with additional "index value-mechanical properties association data" 64 for associating the index values calculated by ultrasonic flaw detection with the mechanical property values, and the rest of the system is the same as the system shown in FIG. 7. As for one example of such processing, arithmetic processing should be executed according to the process flow shown in FIG. 12, which is described below. FIG. 13 is a schematic view corresponding to FIGS. 9A and 9B and is also described below.

The welded zone is C-scanned and the C-scan data is stored in the received signal storing means and input to a signal processor. The average signal strength of the data corresponding to a particular region (e.g., 1×1 mm) is calculated about each address of the data (step 101). This averaging is conducted because the scattered-type penetrators are distributed over a wide region and it is thus better to use the signal strength in a certain wide region than to use peak values in the micro regions to conduct evaluation. Moreover, since the signal strength is practically averaged in the ultrasonic beam width region, it is preferable to set the lower limit of the region to be averaged to be the ultrasonic beam width. The upper limit is the thickness of the pipe. It should be noted that the region to be averaged need not have the same dimensions in vertical and horizontal directions and may be an oblong region. Although the size of the region to be averaged is expressed in terms of actual size (mm) at the welded surface, in actual signal processing means, the data in the memory is referenced. Thus, the actual size is converted into a data point (pixel count) on the basis of the data pitch (pixel size if an image is involved) measured and stored, so as to conduct arithmetic processing.

The average values calculated in step 101 are stored in the average value data memory (step 102). Although not illustrated in FIG. 11, this average value data memory is a two-dimension memory capable of storing the average values of signal strength in association with the pipe axis and pipe thickness, as with the memory for storing the C-scan data of the received signal storing means 56, and typically has the same configuration as the received signal storing means 56. This average value data memory may be a storage region that can be disposed inside the signal processing means 58 or may be an accessible external memory.

The processes of step 101 and step 102 are repeated by shifting the region to be averaged in FIG. 13 in the pipe thickness direction and the pipe axial direction until every pixel in the pipe axial direction and the pipe thickness direction is analyzed (step 103). In actual arithmetic processing, the steps may be repeated by incrementing or decrementing the pixels in the two directions, namely, the pipe axial and pipe thickness directions.

In step 103, after all pixels have been processed, the average data memory is referenced, and the maximum value in the thickness direction is calculated at the same position in the pipe axial direction (step 104). In FIG. 13, this corresponds to the distribution diagram, "Maximum value in the pipe thickness direction". The data is stored in the pipe thickness maximum value data memory (step 105). This pipe thickness maximum value data memory maybe any memory (storage region) capable of storing the maximum value data in association with the positions in the pipe axial direction and may be disposed in the signal processing means 58 or may be an accessible external memory.

The processes of step 104 and step 105 are repeated for all data in the pipe, axial direction (step 106).

Upon completion, the pipe thickness maximum value data is input from the pipe thickness maximum value data memory and the average value is calculated for every particular range (distance) in the pipe axial direction (step 107). The particular range for calculating the average value is preferably the range equal to the size of the specimen used in the Charpy impact test for evaluating mechanical properties.

The mechanical property values are calculated by using the calculated average values as the index values (step 108). As shown in FIG. 10, the mechanical property values may be determined by preliminarily determining the correlation between the mechanical property values and the index values and then obtaining an equation, table data, or the like (this is equivalent to the "Index value-mechanical properties association data 64" in FIG. 11) that can be used to yield the mechanical property values (this is equivalent to −40° C. absorption energy in FIG. 10) from the index values. For example, the table data used to convert the index values to the mechanical property values may be stored in the storing means in the signal processing means and referred.

Note that the processes of calculation are not limited to those described above. For example, in calculating the pipe thickness maximum value data, the region to be averaged may be shifted in the pipe thickness direction while keeping the same position in the pipe axial direction, and the maximum value may be updated in calculating the average value. In such a case, the averaging data memory described above is not necessary.

As described above, it has been found that it is possible to evaluate the quality on the basis of the index values calculated by processing the measurement results of C-scan. However, quality evaluation by C-scan is only possible for samples prepared by cutting out welded zones. Tandem flaw inspection described below can be conducted directly on steel pipes, and the present invention is equally applicable to a detection technique that can conduct quality evaluation of pipes directly.

Figure 14:
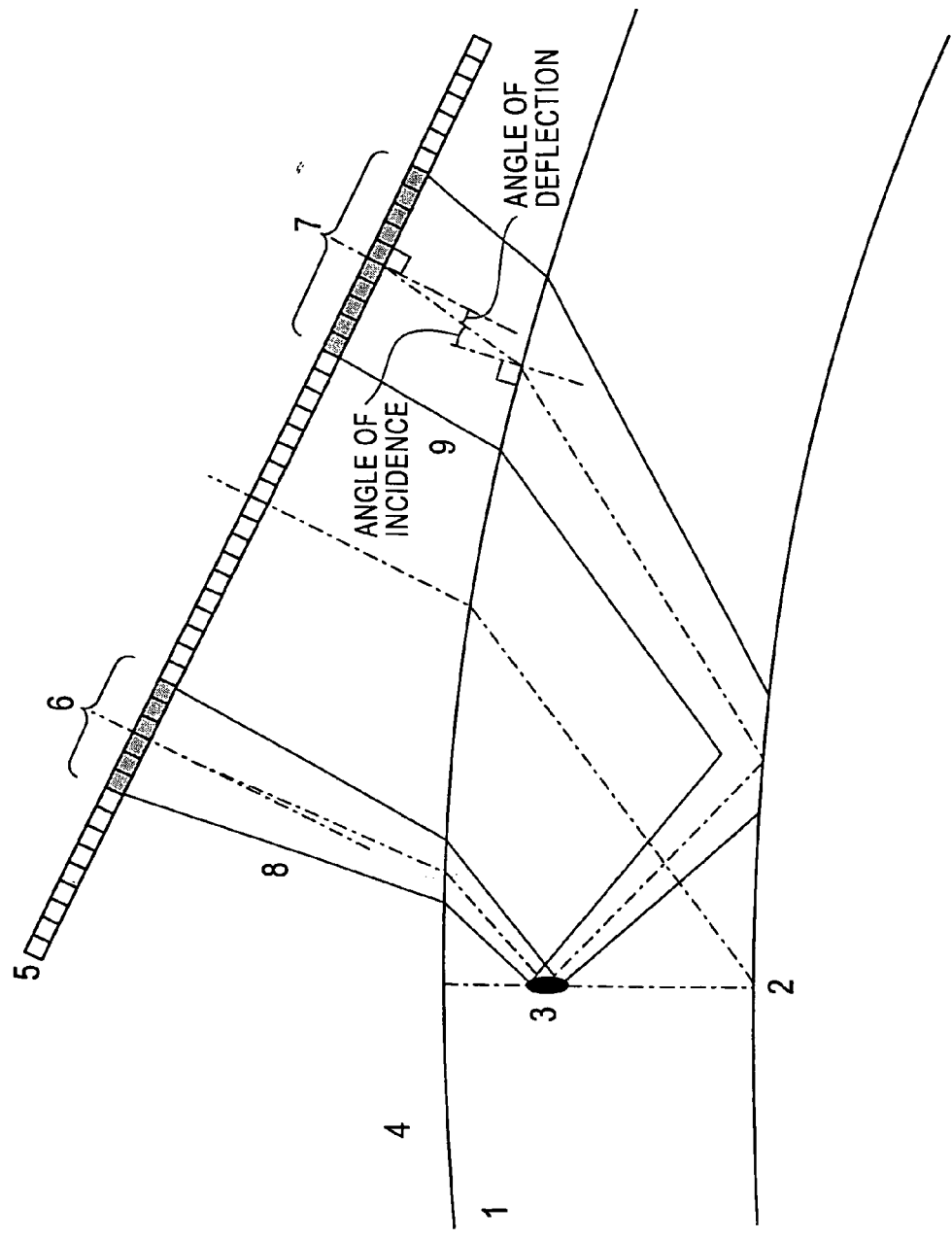
FIG. 14 is a diagram showing the principle of a tandem technique.
Figure 15A:
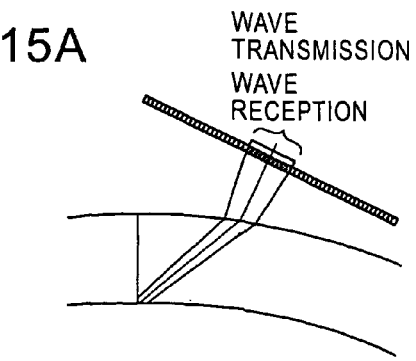
FIGS. 15A to 15D are diagrams showing an example procedure of scanning by a tandem technique.
Figure 15B:
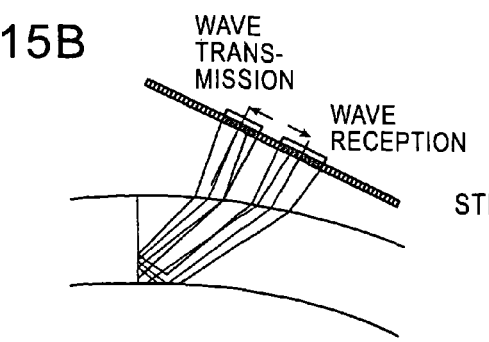
Figure 15C:
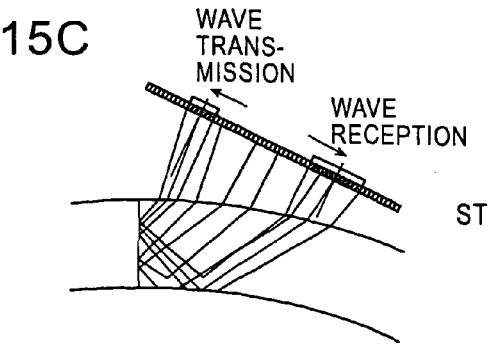
Figure 15D:
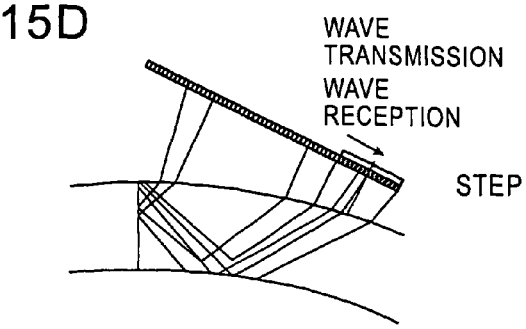

FIG. 14 is a diagram illustrating the principle of tandem flaw inspection. In the drawing, reference numeral 1 represents a steel pipe, i.e., a work to be inspected, 2 represents a welded zone, 3 represents a midwall defect, 4 represents water through which ultrasonic waves are transmitted, 5 represents a linear array probe, 6 represents a transmitter transducer group, 7 represents a receiver transducer group, 8 represents a transmission beam, and 9 represents a part (hereinafter referred to as "reception beam") indicating the ultrasonic wave travelling toward the receiver transducer group from the flaw). The lines respectively drawn at the centers of the transmission beam 8 and the reception beam 9 respectively indicate scanning lines.

The linear array probe 5 has a size such that the ultrasonic waves transmitted from the transducer group located near the welded zone 2 (the left-hand side in FIG. 14) directly enter the steel pipe outer surface of the welded zone and ultrasonic waves transmitted from a transducer group located remote from the welded zone enter the steel pipe outer surface after being reflected once at the steel pipe inner surface. The array probe is also arranged so that the transmission beam emitted from the center in a perpendicular direction is obliquely incident on the outer peripheral surface of the steel pipe, for example, that the transmission beam is incident on the outer surface side of the steel pipe by forming transverse waves with a refractive angle of 45° and enters the steel pipe inner surface-side end portion of the welded zone (0.5 skip).

The ultrasound beam from the transmitter transducer group 6 is slightly deflected toward the central axis side of the array probe to adapt to the outer diameter of the steel pipe so that the refractive angle is 45°, and the delay time is set for each transducer so that the beams are focused at positions that traverse the welded zone 2. Similarly, the receiver transducer group 7 is selected to receive the reflected echo from the flaw 3 as a once-reflected-waves at the inner surface side. The directivity is slightly deflected toward the central axis side of the array probe to adapt to the outer diameter of the steel pipe so that the refractive angle is 45°, and the delay time is set for each transducer so that the beams are focused at positions such that the beams transverse the welded zone 2. Here, the refractive angle is not limited to 45° and an angle in the range of 30° to 70° in which flaw detection with transverse waves is possible can be applied. Considering the angle dependence of acoustic reflectivity of transverse waves being reflected at the flaw and inner surface, the refractive angle is preferably in the range of 35° to 55° in which total reflection is achieved. The range may be 40° to 50° when stability is considered.

As described above, since the numbers and positions of the transducer groups for transmission beams and reception beams and the refractive angle are set so that the beams are focused at the position of the welded zone and the reflected waves from the flaw can be received, reflection from a minute flaw inside the pipe wall can be detected.

An example of a procedure for scanning a welded zone from the steel pipe inner surface to the outer surface will now be described with reference to FIGS. 15A to 15D. First, in step 1 in which scanning begins, a transducer group near the center of a linear array probe is used so that the focusing position (focal position) comes at the steel pipe inner surface side of the welded zone, and flaw detection is conducted by a 0.5-skip reflection technique. Here, transmission and reception are conducted by using the same transducer group. Next, in step 2, the transmitter transducer group is shifted toward the welded zone and the receiver transducer group is shifted away from the welded zone so that the focal position is set to be slightly above the steel pipe inner surface side of the welded zone (steel pipe outer surface side). In this manner, flaws inside the wall and slightly above the steel pipe inner surface side of the welded zone (steel pipe outer surface side) can be detected by tandem flaw inspection.

Subsequently, in step 3, the transmitter transducer group is shifted toward the welded zone side and the receiver transducer group is shifted to the side opposite to the welded zone so that the flaw detection position in the welded zone is moved toward the steel pipe outer surface side, and flaw detection is conducted. Although only steps 2 and 3 are illustrated in the drawings, in practice, the size of the focus of the ultrasonic wave (the beam width at the focal position) is taken into account, and the distance in terms of the number of transducers by which the transducer group is shifted is determined so that there is a partial overlap between ultrasonic beams to achieve efficient flaw detection free of oversight (omission) and redundancy. Finally, step 4 shows the end of scanning where a transducer group remote from the welded zone is used to conduct flaw detection on the outer surface side of the welded zone by a 1.0-skip reflection technique. Steps 1 to 4 are repeated while the relative position of the steel pipe and the linear array probe is mechanically scanned in the pipe axial direction so that flaw detection is carried out over the entire surface and entire length (from the outer surface side to the inner surface side of the steel pipe) of the welded zone.

Figure 16:
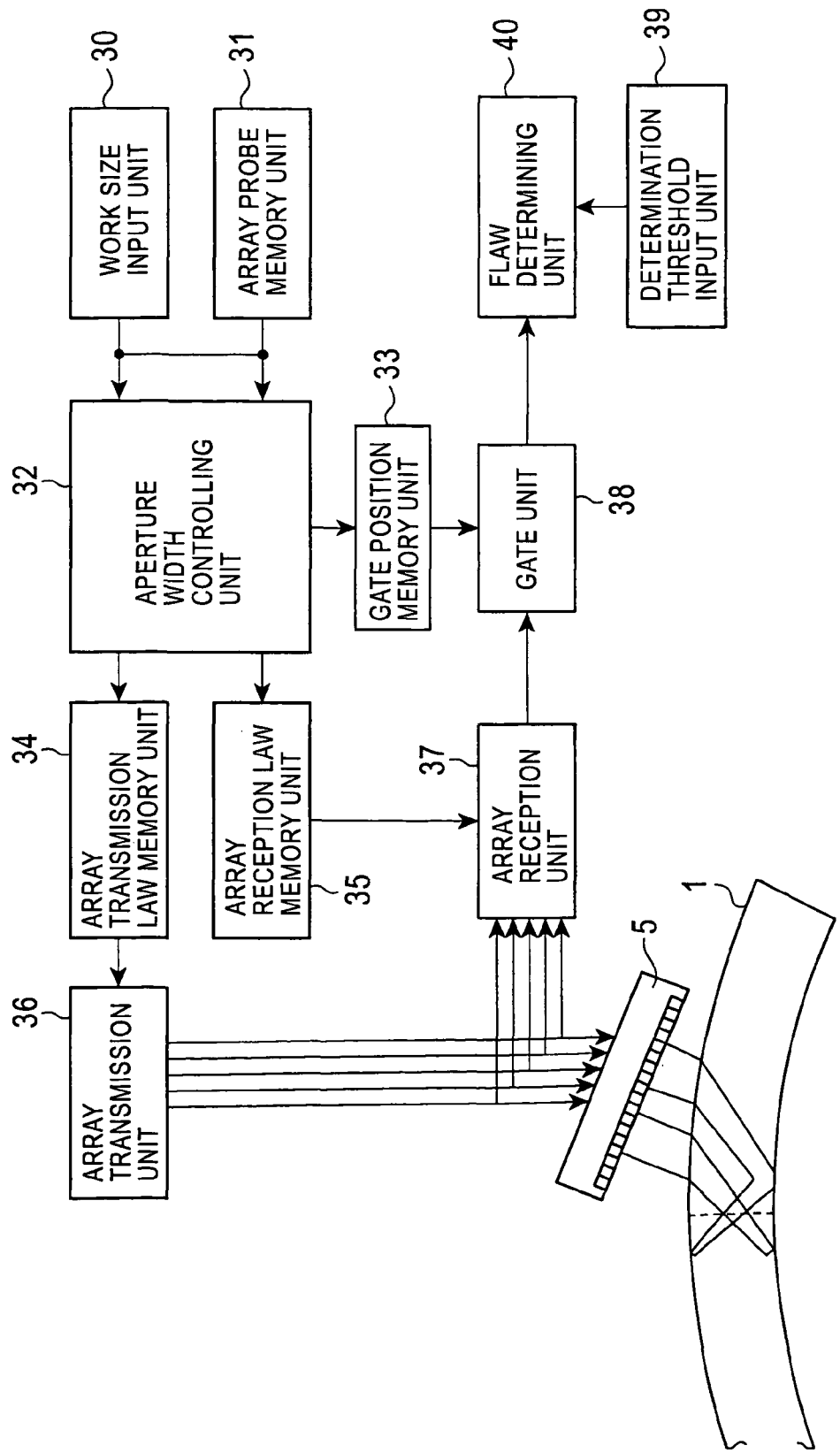
FIG. 16 is a diagram showing a functional structure example of an ultrasonic flaw detector to which a tandem technique is applied.

FIG. 16 is a diagram showing one example of a functional configuration of an ultrasonic flaw detector related to tandem flaw inspection. In a work size input unit 30, the outer diameter and thickness of the steel pipe subject to flaw detection are input through an operator or a process computer. In an array probe memory unit 31, the frequency of the array probe 5, the transducer pitches, and the number of transducers are stored.

In an aperture width controlling unit 32, the aperture width corresponding to the beam size for transmission and reception is controlled, and the position of the transmitting array probe, the number of transmitting scanning lines, and the path of the transmission beam of each scanning line is calculated on the basis of the size of the steel pipe and the specifications of the array probe. Next, for each path, the focal length and deflection angle are determined. The focal length and the ultrasonic wave frequency are then substituted into equation (1) described below to determine the aperture width that yields a beam width within a particular range. As for the particular range of the beam width, the range of 0.5 mm to 2.5 mm is the applicable range and the range is preferably more than 0.7 mm and not more than 2.5 mm, and more preferably, 1.0 mm to 2.0 mm, as described below.

The aperture width is divided by the transducer pitch and the number of transducers in the transmitter transducer group of each scanning line is determined. Then the position of the transmitter transducer group, the focal length, and the deflection angle are determined and calculated from the scanning line position and the number of transducers, and the delay time for each transducer is calculated for every scanning line. Here, these values determined as such are referred to as array transmission rule.

Also in the aperture width controlling unit 32, the position of the array probe, the number of receiver scanning lines, and the path of the reception beam of each scanning line are calculated on the basis of the size of the steel pipe and the specifications of the array probe. Next, the focal length and the deflection angle of each path are determined. The focal length and the ultrasonic wave frequency are substituted into equation (1) described below to determine the aperture width that yields a beam width in a particular range. As with the case of transmission, the applicable range of the beam width for the reception waves is 0.5 to 2.5 mm, and the particular range is preferably more than 0.7 mm and not more than 2.5 mm and more preferably 1.0 to 2.0 mm.

The aperture width is divided by the transducer pitch and the number of transducers in the receiver transducer group of each scanning line is determined. Then the position of the receiver transducer group, the focal length, and the deflection angle are determined and calculated from the scanning line position and the number of transducers, and the delay time for each transducer is calculated for every scanning line. Here, these values determined as such are referred to as array reception rule. The gate position for flaw detection is determined on the basis of the beam path calculated in the aperture width controlling unit 32 and stored in a gate position memory unit 33.

It should be noted here that the array reception rule may be determined on the basis of the array transmission rule previously determined, or, conversely, the array reception rule may be determined first and the array transmission rule may be determined on the basis of the array reception rule. The array transmission rule and the array reception rule determined as such are respectively stored in an array transmission rule memory unit 34 and an array reception rule memory unit 35 and used in transmission/reception control described below.

In an array transmission unit 36, a transmitter transducer group is selected on the basis of the array transmission rule stored in the array transmission rule memory unit 34, and transmission pulses are generated from individual transducer elements with delay times. In an array reception unit 37, a receiver transducer group is selected on the basis of the array reception rule stored in the array reception rule memory unit 35. A signal is added to each element with a delay time to obtain a flaw detection waveform. In a gate unit 38, the gate position signal stored in the gate position memory unit 33 is retrieved.

Upon completion of the flaw detection for one scanning line, the next transmitter transducer group is selected on the basis of the array transmission rule stored in the array transmission rule memory unit 34, and flaw detection is repeated as described above.

Note that for the pipe axial direction, the conditions under which the array probe and the welded steel pipe can move relatively should be set. For example, when the flaw detection is incorporated in a manufacturing process in which the welded steel pipe travels in the pipe axial direction, the pipe can be scanned in the pipe axial direction by affixing the array probe and conducting scanning in the pipe thickness direction. If the welded steel pipe is stationary, the array probe may be moved using a mechanical mechanism.

In a flaw determining unit 40, a flaw determining threshold input to a detection threshold input unit 39 is compared with the signal strength in the gate, and presence of a flaw is determined if the signal strength is equal to or more than the threshold.

An embodiment of a quality control method of the present invention employing tandem flaw inspection will now be described.

Figure 17:
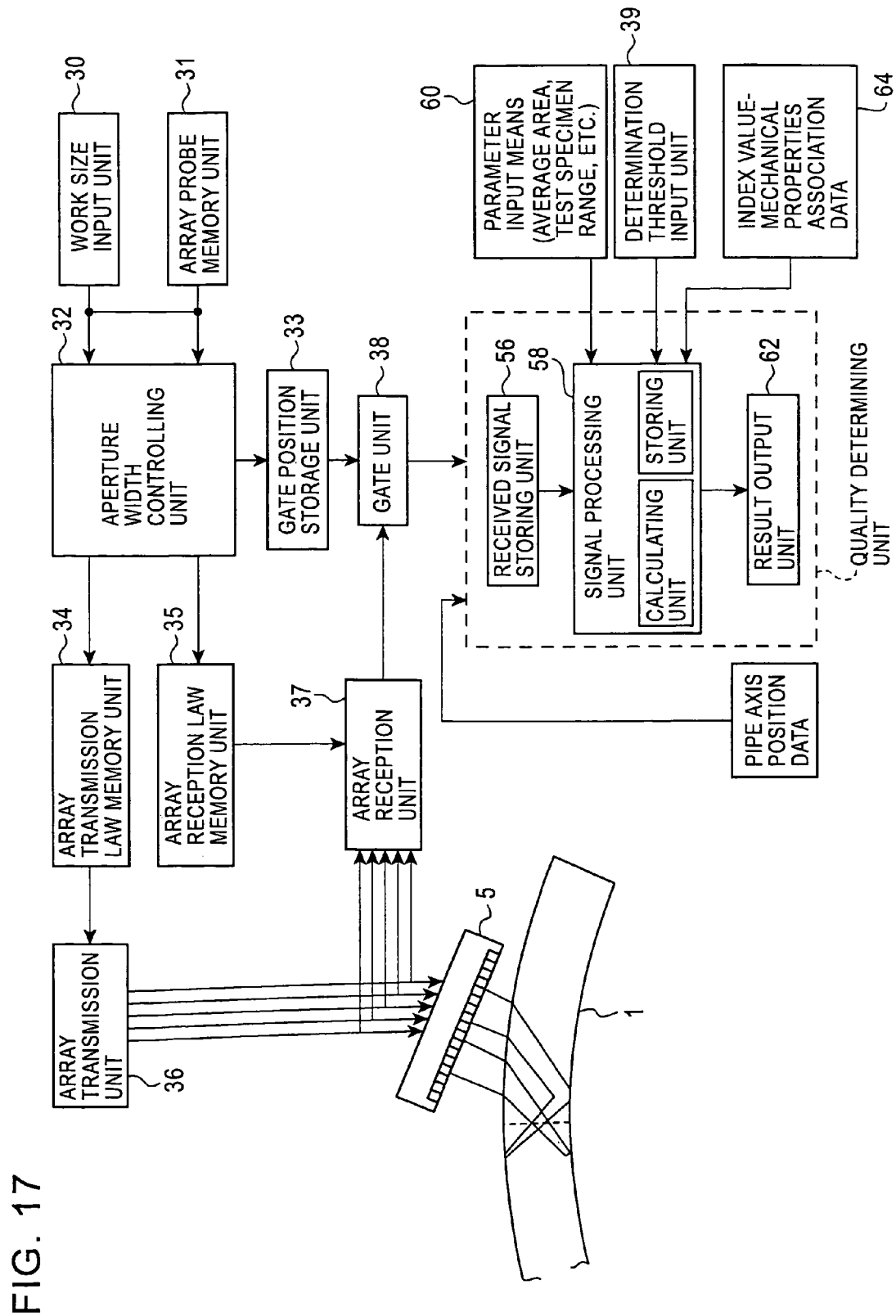
FIG. 17 is a diagram showing a functional structure example in which a tandem technique is applied to the present invention.

In particular, a system shown in FIG. 17 may be used. In this system, the configurations in the peripheries of the flaw determining unit 40 shown in FIG. 16 are changed. The system additionally includes means having the same functions as the received signal storing means 56, the signal processing means 58, the parameter input means 60, and the result output means 62 shown in FIG. 11. The process flow shown in FIG. 18 may then be executed.

In FIG. 11, the received signal storing means 56 stores the received signal strength (C-scan data) associated with the position of the probe 50 moved. In contrast, because the system shown in FIG. 17 involves tandem flaw inspection in which the transducer groups of the array probe are controlled to scan the welded zone in the pipe thickness direction while scanning and measuring the welded zone in the pipe axial direction by relative positional shifting, data related to the operation position in the pipe thickness direction (e.g., the setting value set by the controlling unit) and the position of the steel pipe in the pipe axial direction (e.g., the travelling distance on the line) is input, and the values are converted into the position in the pipe thickness direction and the pipe axial direction and stored. As a result, as in the case of C-scan, a received signal can be associated with the pipe axial direction and the pipe thickness direction and stored in the received signal storing means while leaving the steel pipe as is. Thus, the on-line, in-line quality control is possible in the manufacturing process.

Figure 12:
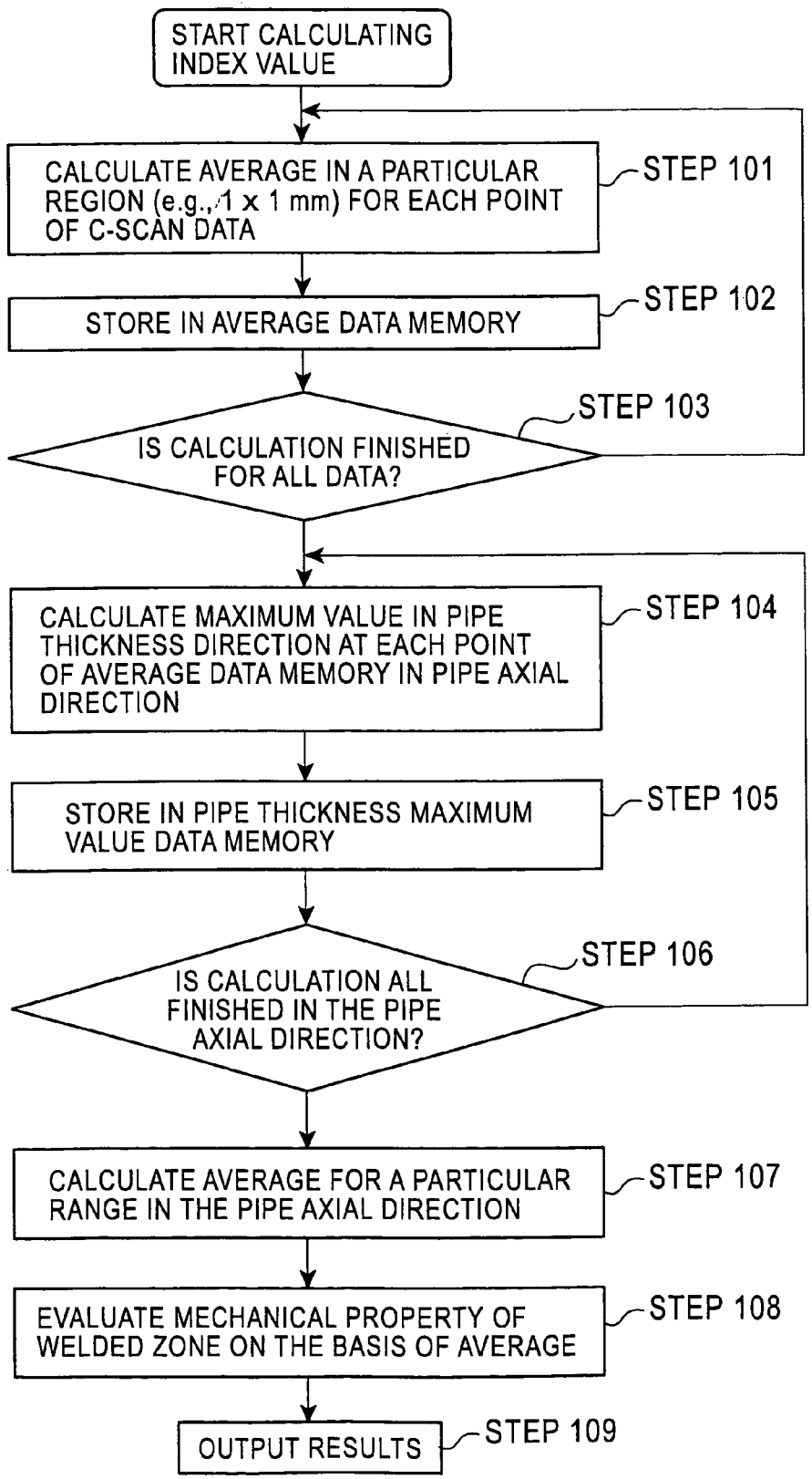
FIG. 12 is a diagram showing a data processing flow of the present invention to which C-scan is applied.
Figure 13:
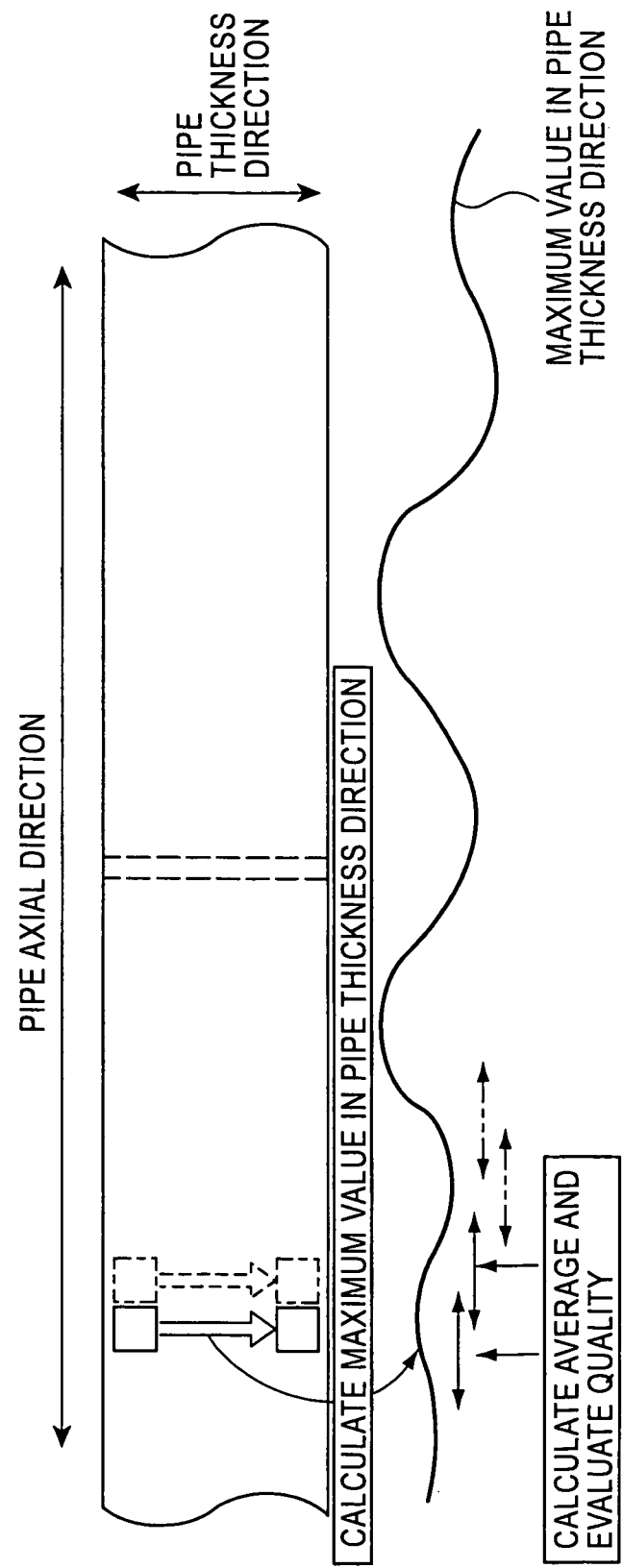
FIG. 13 is a diagram showing one example of scanning a predetermined area according to the present invention.
Figure 18:
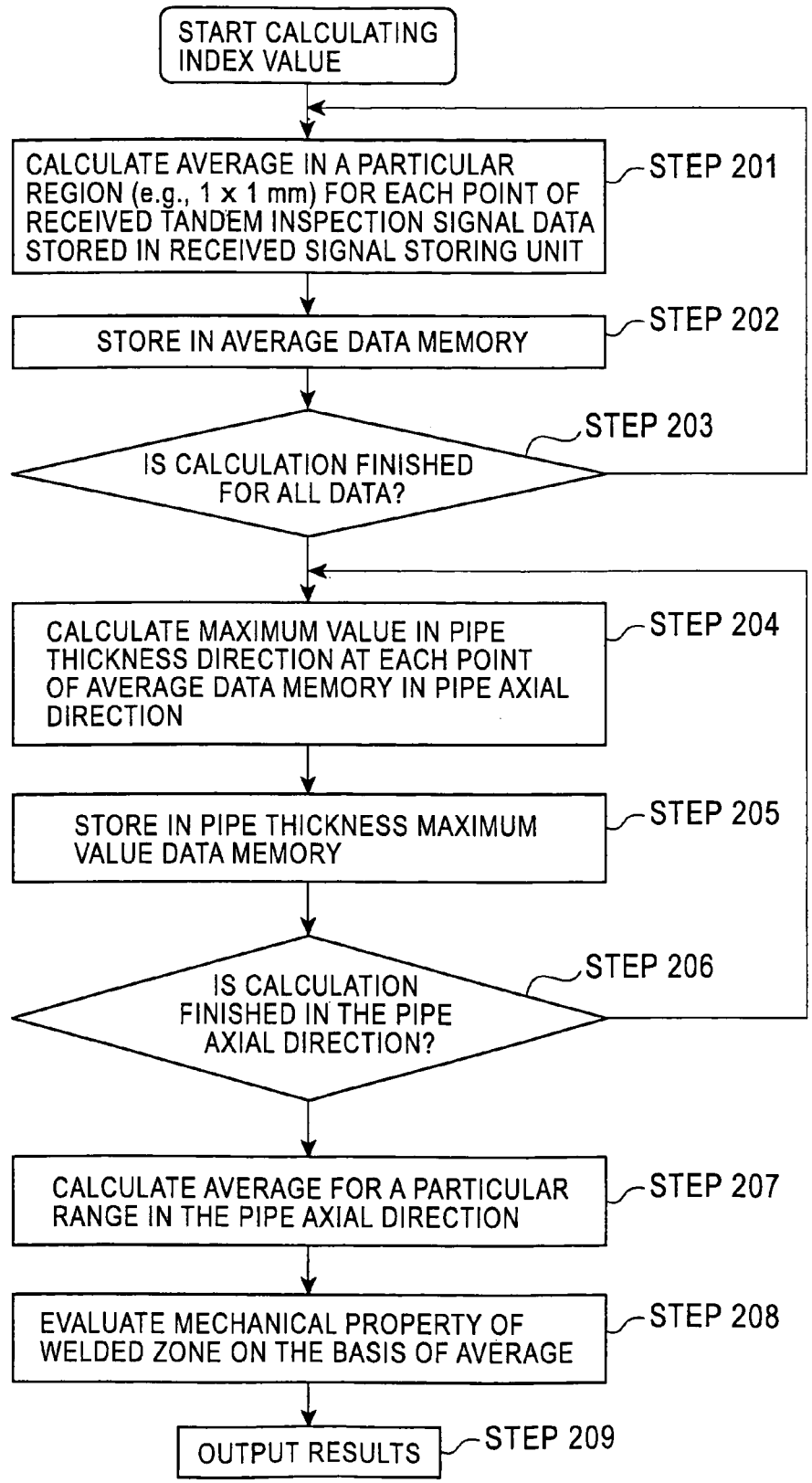
FIG. 18 is a diagram showing a data processing flow according to the present invention to which a tandem technique is applied.

Explanation of FIG. 18 is omitted here since the only difference is that, in step 201, signal strengths received in the array reception unit of tandem flaw inspection are referenced whereas C-scan data is referenced in step 101 of FIG. 12 and since step 202 and subsequent steps are the same as step 102 and subsequent steps shown in FIG. 12.

As described above, the mechanical properties of the welded zone of a welded steel pipe as is can be evaluated through ultrasonic flaw detection by using results obtained by tandem flaw inspection. Since tandem flaw inspection makes it possible to detect flaws in the welded zone of a steel pipe as is, tandem flaw inspection can be incorporated in an electric resistance welded steel pipe production process and can be used in quality administration and quality control.

Figure 19:
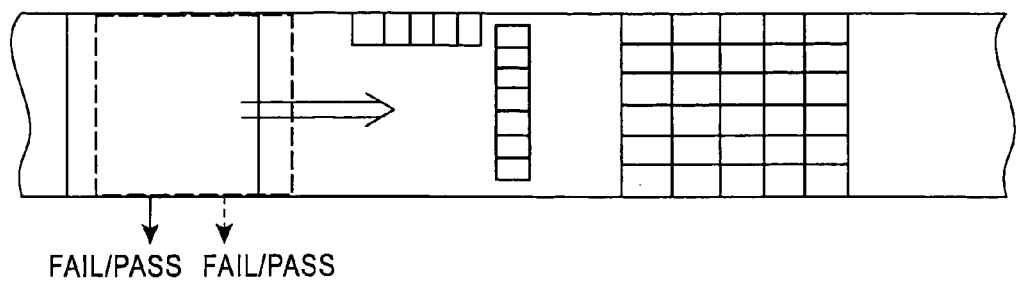
FIG. 19 is a diagram showing another example of scanning the predetermined area according to the present invention.

In both the tandem flaw inspection and the C-scan technique, the unit area in which the average value is calculated may be a small unit area shown in FIGS. 9A, 9B, and 13 scanned in the pipe thickness direction and the pipe axial direction, or may be a region elongated in the pipe axial direction or pipe thickness direction as shown in FIG. 19 depending on the distribution state of the penetrators, or may take any adequate shape and size. For example, if the penetrators are distributed widely over the entirety, a relatively large unit area may be designated.

Figure 20:
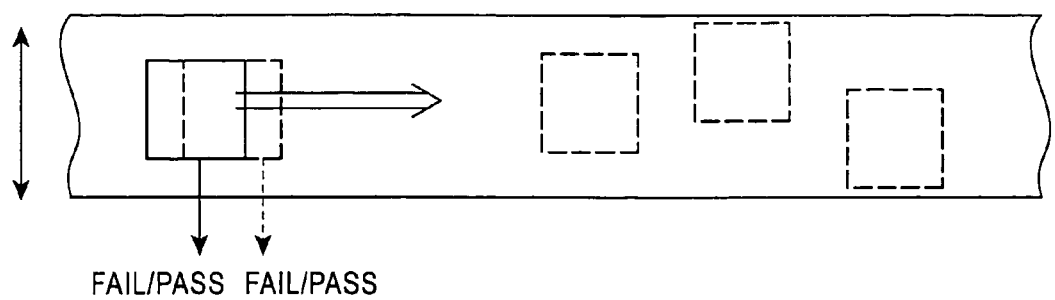
FIG. 20 is a diagram showing yet another example of scanning the predetermined area.

In the case where it is known that the penetrators are concentrated in a particular part in the pipe thickness direction, a range in the thickness direction may be set relative to the range where concentration is occurring instead of the entirety in the pipe thickness direction as shown in FIG. 20, the average value in that range may be determined, and the measurement may be conducted by moving the probe only in the pipe axial direction by the unit area.

In conducting the averaging process, the calculation method is not particularly limited, e.g., the average in the region may be simply calculated, the average may be taken with different weights on different positions, or an exponential moving average technique may be employed. During calculation, it is not necessary to conduct the process at a pixel pitch/(measurement pitch) stored in the data memory. The pixel pitch for use in calculation may be set according to the required spatial resolution and accuracy.

Moreover, as a matter of course, the calculation procedure is not limited to the procedure described above and any calculation that can achieve the same effects and advantages may be used.

This ends the description for managing the quality of the steel pipe as is by employing tandem flaw inspection. However, various studies have been made to apply the above-described tandem flaw inspection to the welded zones of electric resistance welded steel pipes. Specific details are given below.

Figure 21A:
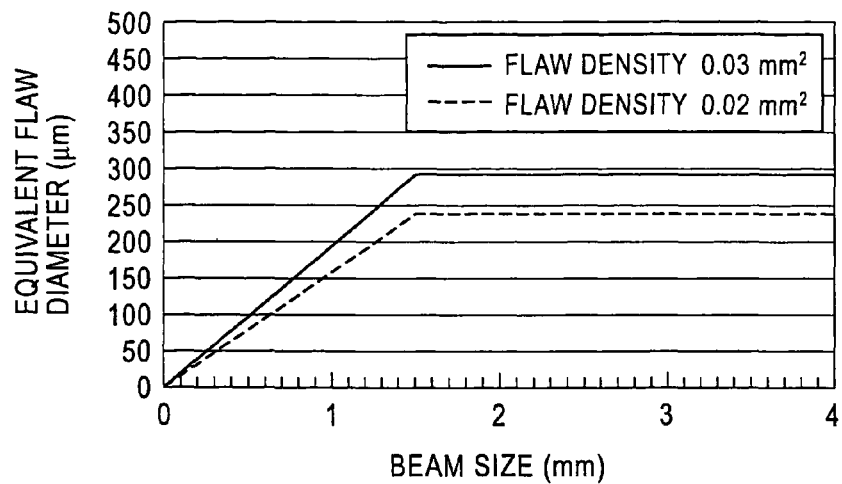
FIGS. 21A to 21C are graphs showing the relationship between the beam size and the signal strength.

First, as for the determination of the aperture width in the aperture width controlling unit 32, the following may be considered. FIG. 21A is a graph showing the relationship between the beam width (beam width corresponding to one side of a rectangle, referred to as "beam size" in FIGS. 21A to 21C) and the equivalent flaw diameter (flaw diameter equivalent to the total flaw area in the beam). The equivalent flaw diameter with a varying beam width (beam size) at a flaw density of 0.03 mm² and 0.02 mm² is theoretically calculated by assuming the total area of flaws present in the ultrasonic beam to be the equivalent flaw diameter. As the beam width increases, the equivalent flaw diameter increases. At a beam width of 1.5 mm or more, the equivalent flaw diameter is saturated and takes a constant value. The reason for such saturation is that, for the purposes of this analysis, the distribution range of the scattered-type penetrators is assumed to be 1.5 mm×1.5 mm.

Figure 21B:
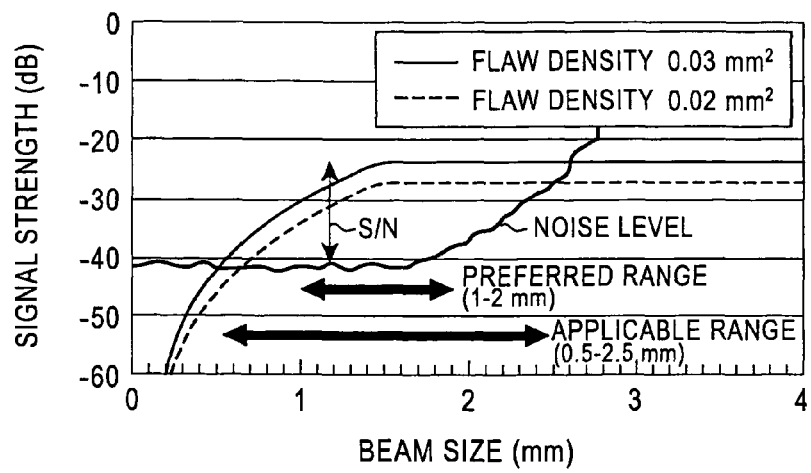

FIG. 21B is a graph showing the signal strength in dB calculated on the basis of the acoustic reflectivity corresponding to the equivalent flaw diameter shown in FIG. 21A in tandem flaw inspection. The noise level, −40 dB, is a rough figure of the level actually obtained by the tandem technique. The noise level increases as the beam width (beam size) increases because, as the beam width increases, the noise attributable to surface roughness of the inner and outer surfaces is detected and this increases the noise level. It can be understood that, in tandem flaw inspection, the beam width range of 0.5 to 2.5 mm in which the noise level is smaller than the signal level is the applicable range. At a flaw density of 0.02 mm², the signal strength is slightly low. Thus, the beam width of more than 0.7 mm and not more than 2.5 mm is the applicable range; moreover, in order to yield a good S/N ratio, the range of 1 to 2 mm is preferable since the difference between the signal level and the noise level is desirably 5 dB or more.

Figure 21C:
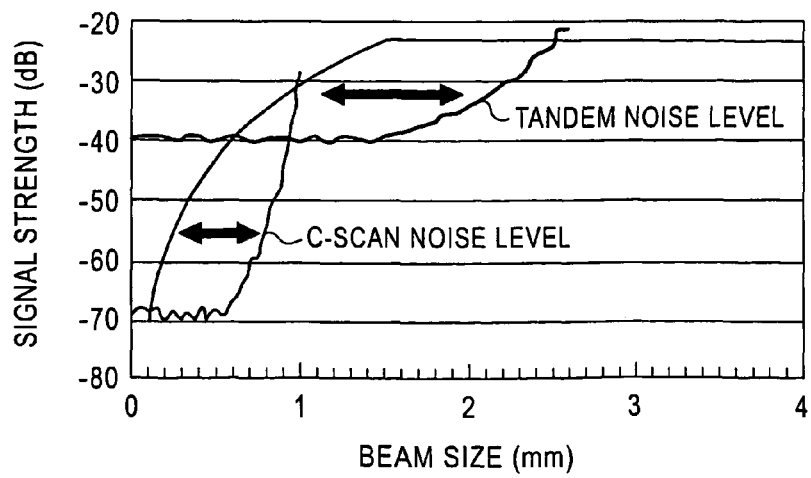

FIG. 21C is a graph showing the signal strength in dB of the equivalent flaw diameter described above, in which the tandem flaw inspection and the C-scan are compared. In FIG. 21C, only the signal levels at a flaw density of 0.03 mm² are shown. In the case of C-scan, the signal strength is higher than the noise level in the beam width range of 0.2 to 1 mm; thus, this range is the applicable range for detecting the scattered-type penetrators. In the description above, the beam width is set to 440 μm in the embodiment employing C-scan in FIG. 8.

This is because the difference between the signal strength and the noise level is the largest at this beam width and the S/N is at a preferable level. The reason why the applicable range differs between the C-scan and the tandem flaw inspection is that, the C-scan has various preferable conditions such as single probe, a shorter water distance, and polished surfaces, and thus exhibits a noise level lower than in the case of tandem flaw inspection. In contrast, when the beam size exceeds 1 mm, the S/N deteriorates due to the side surfaces of the sample (i.e., the beam propagation path is blocked and scatter reflections occur at the sample side surfaces, creating noise signals that are picked up).

Thus, in the case of tandem flaw inspection, the aperture width is set so that the beam width is different from that used in C-scan.

In tandem flaw inspection, the aperture width D of transducers for obtaining the beam width d can be determined from the following equation:

$$D = \lambda \cdot \frac{F}{d \cdot \sin\theta} \cdot \frac{\cos\theta w}{\cos\theta} \qquad (1)$$

Figure 22:
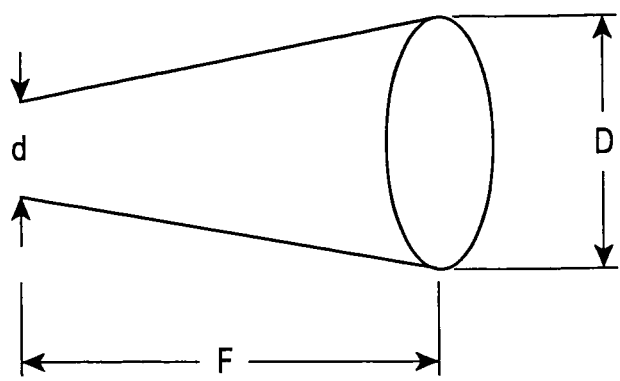
FIG. 22 is a diagram showing the relationship between the aperture width and the beam size.

In the equation, d represents the beam width at a flaw inspection position and F represents the focal length as shown in FIG. 22; $\lambda$ represents the wavelength; $\theta$ represents the refractive angle; and $\theta w$ represents the angle of incidence.

For example, when the water distance is 30 mm, the travel path length in the steel is 24 mm, the refractive angle $\theta$ is 45°, and the angle of incidence $\theta w$ is 18.9°, the focal length F is 30+24/1480×3230=82 mm and the wavelength $\lambda$ at 10 MHz is 1480/10 MHz=0.148 mm. Thus, the aperture width D for achieving beam width d=1.5 mm calculated by equation (1) is D=15 mm.

The number of transducers in the transducer group is determined from the aperture width determined as described above. The number of transducers in the transducer group for each scanning line may be constant or, to achieve more uniform sensitivity, may be varied from one scanning line to another. That is, in tandem flaw inspection that uses an array probe, the focal length becomes shorter as the transducer is positioned closer to the welded zone and becomes longer as the transducer is positioned farther from the welded zone. Thus, the aperture width and the number of transducers that are simultaneously vibrated are determined so that the beam width is within the above-described range or is constant while considering the focal length F according to the position of the transducer. Then control is performed so that a number of transducers corresponding to this aperture width are simultaneously vibrated. Here, the "number of transducers that are simultaneously vibrated" refers to the number of transducers in a transducer group used for performing one operation of transmitting or receiving waves. Then, in this transducer group, a delay time is set for each element to control the focusing and deflection.

Figure 23A:
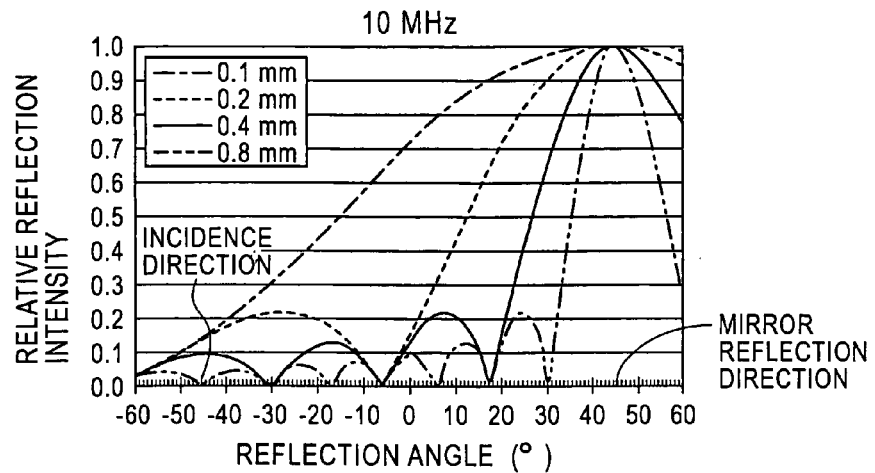
FIGS. 23A to 23C are graphs explaining the relationship between the size of a flaw and the reflection directivity.
Figure 23B:
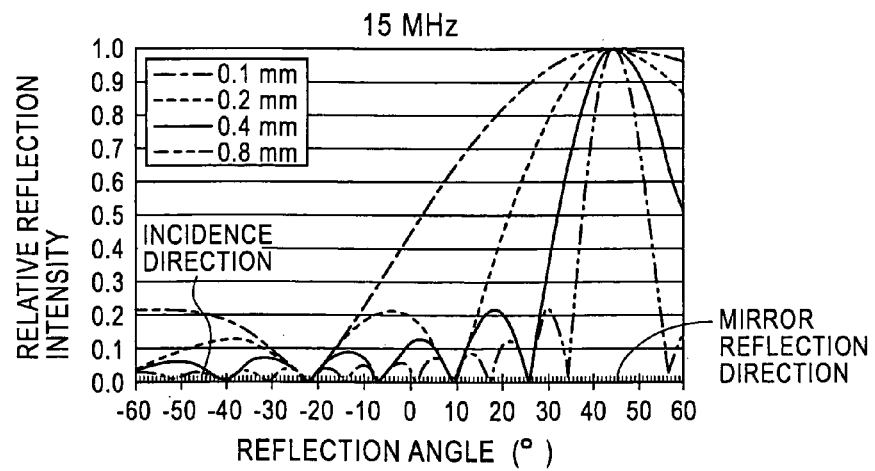
Figure 23C:
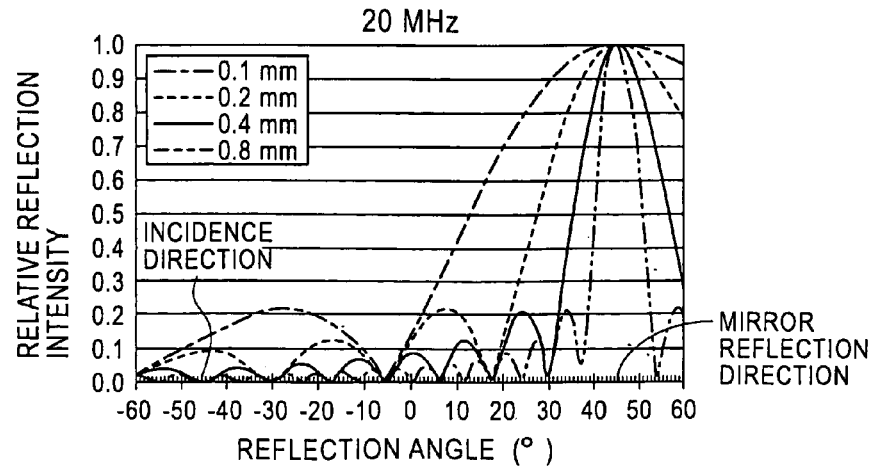
Figure 24:
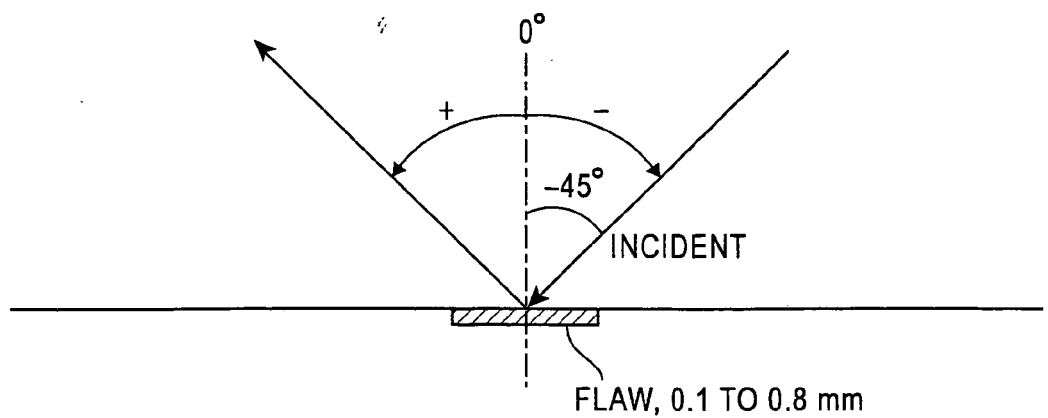
FIG. 24 is a diagram illustrating the reflection property.

The incident angle and reflection angle with respect to the welded surface may be determined as below. FIGS. 23A to 23C show the results of theoretical investigations on the relationship between the size of flaws and the reflection directivity. The results shown in FIGS. 23A to 23C are determined by theoretically calculating the signal strength at each angle of reflection when the ultrasound is incident in the −45° direction at frequencies of 10 MHz, 15 MHz, and 20 MHz and the flaw size (equivalent flaw size) corresponding to the pipe wall thickness direction (corresponding to the transverse direction in FIG. 24) is 0.1 mm, 0.2 mm, 0.4 mm, and 0.8 mm, as shown in FIG. 24. The vertical axes of FIGS. 23A to 23C indicate normalized relative values that assume the signal strength at 45°, i.e., a mirror reflection angle, to be 1. It can be found that in all cases, the signal strength of the reflected waves reflected in the −45° direction in which the ultrasound is incident is very low, i.e., 0.2 or less relative to that in the mirror reflection direction, 45°, and the signal strength is strongest in the 45° direction, i.e., the mirror reflection direction.

Under such calculation conditions, the angle range in which the signal strength is half (0.5 in FIGS. 23A to 23C) the signal strength at the mirror reflection angle is 40° to 50° at 20 MHz for the 0.8 mm flaw size at which the directivity is the steepest. Since the directivity differs depending on the flaw size, the range of the angle of incidence of the reception beam with respect to the welded zone may be determined on the basis of the size of the flaws to be detected. For example, in order to detect larger flaws without degrading the sensitivity, the angle of incidence of the reception beam on the welded zone is preferably close to 45°. For example, in order to suppress the decrease in signal strength for the 0.8 mm flaw to half at 15 MHz, the angle is preferably in the range of 39° to 52°. In contrast, when the detection target is small flaws 0.4 mm or less in size at 15 MHz, the range of 33° to 61° is preferred.

In view of the above-described analysis, the reflected signals of ultrasound reflected at a flaw increases and peaks in the mirror reflection direction. Thus, it is most preferable to receive the ultrasound in the mirror reflection direction. However, detection can be sufficiently carried out at a reflection intensity of 50% of the peak intensity. Thus, the ultrasound reflected in the angle range corresponding to such a range may be received.

In view of the results of reflection directivity for a flaw size of 0.4 mm at a frequency of 15 MHz shown in FIGS. 23A to 23C, the reflection angle at which the reflection intensity is 50% or more of the peak is 33° to 61°. Thus, on the basis of the mirror reflection angle, i.e., 45°, a range of −12° to +16° is the preferred range. When a flaw size up to 0.8 mm is the target at a frequency of 20 MHz, a range of −5° to +5° with respect to the mirror reflection angle is the preferred range. Moreover, in the example described above, the reflection angle characteristics at an angle of incidence of 45° on the flaw are indicated. However, the same incident angle characteristics are obtained if the angle of reflection is set to 45°, and the angle of incidence may be an angle other than 45°. As long as the angle of incidence is within the range that can clear the conditions for mode conversion losses, substantially the same characteristics are obtained.

When the mode conversion loss is considered, the refractive angle suited for flaw inspection with transverse waves is within the range of about 30° to about 70°. When the angular dependency of the acoustic reflectivity of the transverse waves being reflected at the flaw and inner surface is considered, a range of 35° to 55° in which total reflection is achieved is more preferred. The range may be set to 40° to 50° in view of stability. Moreover, the refractive angle of the transmission waves is most preferably the same as that of the reception waves. However, since the reflection directivity of the flaw is broad, they may differ from each other within the range of reflection directivity.

Figure 25:
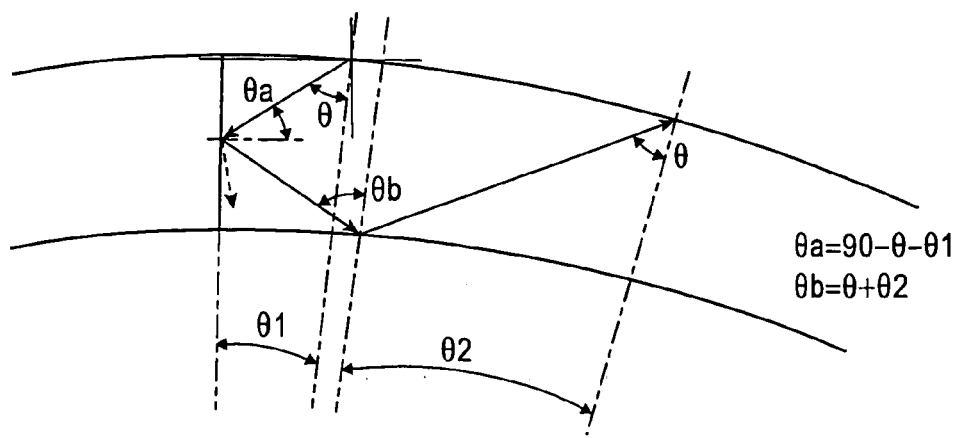
FIG. 25 is a diagram illustrating the mode conversion loss at a steel pipe.

The process for setting the refractive angle range in which no mode conversion losses occur will now be described with reference to FIG. 25.

1) Determine the refractive angle and determine the position and angle of the array probe 1)-1: The refractive angle $\theta$ is determined by considering the angle of incidence $\theta a$ on the welded surface. The theoretical angle of incidence on the welded surface at which no mode conversion losses occur is $33.2° \leq \theta a \leq 56.8°$. As long as the angle is within this range, the angle of incidence on the welded surface need not be constant and may vary during scanning of the welded surface in the pipe thickness direction from the inner surface to the outer surface. Thus, in order to simplify the calculation, an example in which the refractive angle $\theta$ is adjusted to a constant level is discussed here. The angle of incidence $\theta a$ on the welded surface is $\theta a = 90° - \theta - \theta 1$, where $\theta 1$ varies depending on the position in the welded zone thickness direction within the range of 0 to $\theta 2$ (for example, $\theta 1 = \theta 2$ at the inner surface side and $\theta 1 = 0$ at the outer surface side). For example, when $\theta 2 = 4°$ and the refractive angle is 45°, $\theta a = 41°$ to 45°. When the refractive angle at the time the beam enters the vicinity of the center of the welded zone in the pipe thickness direction is set to 47°, $\theta a$ at the vicinity of the center of the welded zone in the pipe thickness direction is about 45°, and $\theta a$ is within the range of 43° to 47° during scanning of the inner and outer surfaces.

1)-2: The position and angle of the array probe are determined so that a beam as a transverse ultrasound, which is transmitted in a direction perpendicular to the probe surface from the transducer at the center of the array probe, enters from the steel pipe outer surface side at a particular refractive angle (e.g., 45° and enters the position of the inner surface-side edge (or outer surface-side edge) of the welded surface at a particular angle of incidence (e.g., 41° in the above-described example).

2) Determine the positions where the scanning lines transmitted from and received by respective transducers of the array probe are incident on the outer surface of the pipe 2)-1: There are various methods for determination. For example, for a target transducer (or a position between transducers), the pipe outer surface is scanned to calculate the refractive angle $\theta$ determined by the position of the transducer, the position of the scanning on the outer surface, and the outer surface tangent line, and the position where $\theta$ is equal to the value determined in 1)-1 is determined. In particular, scanning lines are determined by connecting each transducer to respective points on the outer surface (e.g., these points may be arranged on the outer periphery at regular or arbitrary intervals) with straight lines, the refractive angle $\theta$ for each scanning line is calculated, and the scanning line that has $\theta$ equal to or closest to the particular refractive angle is selected to determine the position of incidence of that scanning line.

2)-2: The propagation paths after the beam is incident on the pipe are geometrically determined on the basis of the position of the transducers, the position of incidence on the outer surface determined in 2)-1 above and the pipe shape (diameter and thickness) to identify the position of incidence on the welded surface.

3) Since positioning is conducted at the center of the array probe as described in 1) above and the above-described process is conducted by assuming the refractive angle to be constant, a combination (pair) of routes of propagation paths (scanning lines) on the welded surface determined by 2)-2 above is formed in a symmetrical manner with respect to the scanning line at the center of the array probe. This pair is assumed to be the scanning line for transmission and the scanning line for reception, and used as center transducers for a transmission unit and a reception unit, respectively (transducer groups for a transmission unit and a reception unit are formed with these transducers at the center). When the number of the transducers in the group is an even number, the center position is corrected to be the boundary between transducers in conducting the process described above. Moreover, although the refractive angle θ is assumed to be constant in this calculation, the angle of incidence θa on the welded surface may be assumed to be constant or both θ and θa may be varied in conducting calculation.

The process of controlling the transducer groups to scan the welded surface in the thickness direction with beams using this ultrasonic flaw detector will now be described. In particular, the transducer groups for transmission and reception, the number of transducers, the deflection angle, and the focal length may be determined by the following process. Here, the refractive angle is constant and the widths of the transducer groups used in a transmission unit and a reception unit may be determined on the basis of the aperture widths determined by the beam width. This is described with reference to FIG. 14. The contents of a), b), and g) are equivalent to 1), 2), and 3) discussed earlier and thus described only briefly.

a) The position of a linear array probe is determined so that the beam as a transverse ultrasound, which is transmitted in a direction perpendicular to the probe surface from the transducer at the center of the linear array probe, enters the steel pipe at a particular refractive angle (e.g., 45° and enters the welded zone at the steel pipe inner surface side or the steel pipe outer surface side.

b) The point of incidence is geometrically determined so that the angle of incidence from each transducer on the steel pipe outer surface is constant or within a particular range, and the line (scanning line) that passes through the steel pipe at a refractive angle of 45° is determined.

Here, "each transducer" means the transducer corresponding to the central position of the transmission unit, and the positional relationship between the transducer group of the transmission' unit and the point of incidence at the steel pipe outer surface is determined. Moreover, the propagation paths after the beam enters the steel pipe, i.e., the point of reflection at the inner surface, the point of reflection at the outer surface, and the point of reflection at the welded surface, are determined according to the refractive angle.

c) The deflection angle of each scanning line is calculated from the positional relationship between the point of incidence and each transducer.

d) The water distance of each scanning line and the path length in the steel up to the welded zone are calculated and converted by the sonic velocity and the water distance to determine the water focal length F.

e) The aperture width D of each scanning line is calculated by using equation (1) to achieve the required beam width d, and the aperture width D is divided by a transducer pitch and the result is rounded to the nearest whole number so as to determine the number of transducers n in a transducer group of each scanning line. The required beam width d is, as described above, the range of beam diameter applied to detect scattered-type penetrators, which are minute flaws that are distributed over a wide region. As discussed earlier, the required beam width d is 0.5 to 2.5 mm, preferably over 0.7 mm to 2.5 mm, and more preferably 1.0 to 2.0 mm.

f) The position of each transducer group constituting the transmission unit is determined on the basis of the transducer position of each scanning line and the number of transducers n.

g) On the basis of the positional relationship of each scanning line intersecting the welded zone, the scanning line used for flaw inspection is determined and the transducer group for reception which pairs with the transducer group for transmission is determined. The selection of the pair of the transmission unit and the reception unit may be made by paring two scanning lines that propagate in opposite directions and intersect at the welded zone. If too many pairs intersect the same position of the welded zone with respect to the required spatial resolution, some of the pairs may be left unused.

h) Since the number of transducer groups, the focal length, and the deflection angle are determined for every scanning line used for flaw inspection, the delay time given to each transducer is calculated. For this calculation method, a known technique disclosed in Japanese Unexamined Patent Application Publication No. 4-274756 filed by the present inventors prior to this application may be used.

Figure 26:
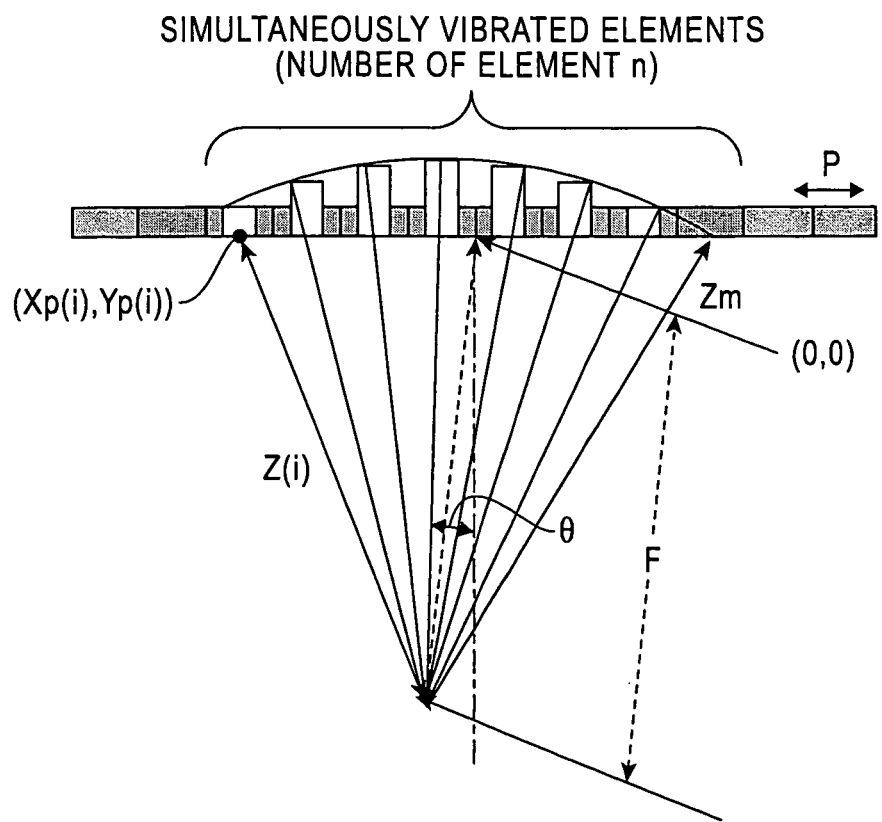
FIG. 26 is a diagram/illustrating calculation of the delay time given to each transducer.

The basic concept of the calculation is described below with reference to FIG. 26 and equations. First, the coordinate of the focal point {Xf, Yf} is determined as follows where the center position of a transducer group is assumed to be the origin of the coordinate, the focal length is represented by F, and the deflection angle is represented by θ:

$$Xf = F \cdot \sin\theta,\ Yf = -F \cdot \cos\theta$$

Next, the coordinate of each transducer, {Xp(i), Yp(i)}, is determined as follows where the transducer pitch is represented by P, and the number of transducers (simultaneously vibrated elements shown in FIG. 26) is represented by n:

$$Xp(i) = -n \cdot p/2 - p/2 + p \cdot i,\ Yp(i) = 0\ (i=1\text{ to }n)$$

The focal position, the distance Z(i) to each transducer, and the maximum distance Zm are determined as follows:

$$Z(i) = SQRT\{(Xf - Xp(i))^2 + (Yf - Yp(i))^2\}\ (i=1\text{ to }n)$$

$$Zm = \max\{Z(i)\}\ (i=1\text{ to }n)$$

Lastly, the delay time Δt(i) is determined by the following equation where C represents sonic velocity:

$$\Delta t(i) = (Zm - Z(i))/C\ (I=1\text{ to }n)$$

The above description shows the basic concept of calculation and there is no need to make the center position of the transducer group the origin of the coordinate for each scanning line. Moreover, although the number of transducers n described is an even number, it may be an odd number. Naturally, when the number is an odd number, the equations described above can still be applied by being partly modified. In actual calculation, the coordinates of the respective elements of the array probes may be determined in advance, the coordinate of the focal position may be determined on the basis of the focal length and the deflection angle, and the distance Z(i) between the focal point and each transducer may then be determined.

Figures 27A, 27B:
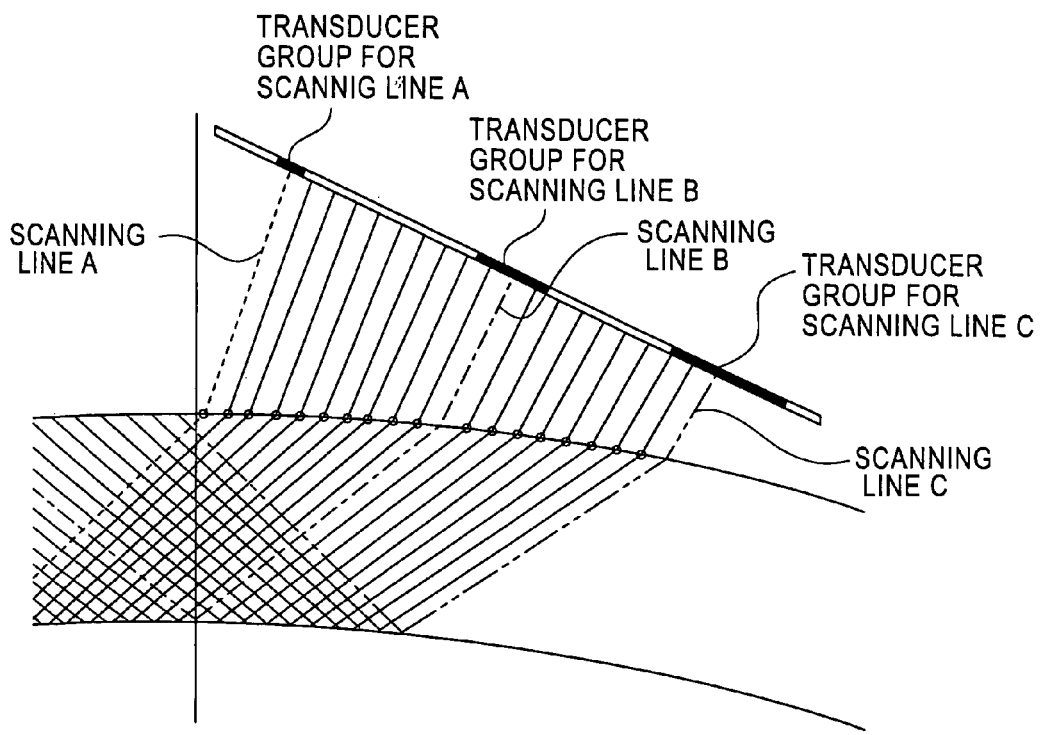
FIGS. 27A and 27B are diagrams showing scanning lines and one example of results of calculation of flaw detection conditions at representative points.

FIGS. 27A and 27B show scanning lines determined as such and one example of results of calculation of the flaw detection conditions at representative points on the scanning lines. In this example, a steel pipe with an outer diameter of 558.8 mm and a thickness of 25.4 mm is inspected with a linear array probe including 160 elements (transducers) arranged at a 0.5 mm pitch at an ultrasonic wave frequency of 15 MHz with a water distance of 20 mm at the center and a refractive angle of 45°. As for the transducer numbering, a transducer closest to the welded zone is numbered 1 and a transducer farthest from the welded zone is numbered 160.

Figure 28A:
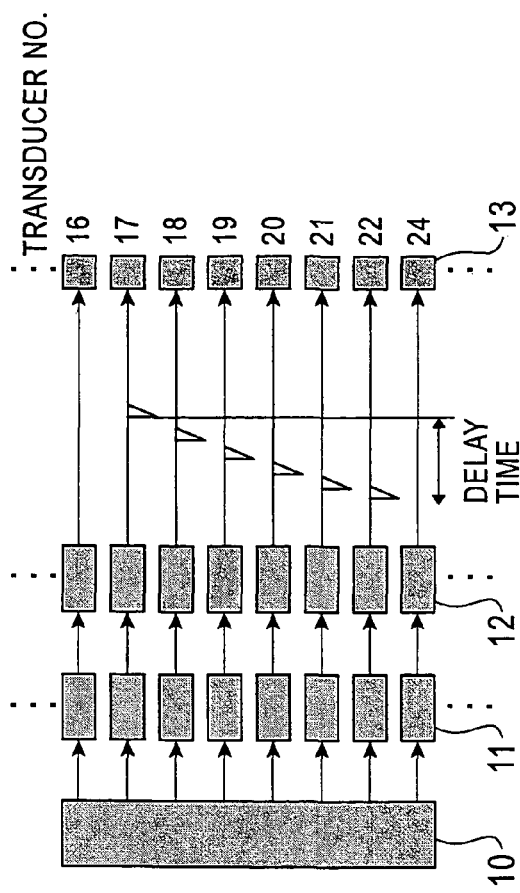
FIGS. 28A and 28B are diagrams showing the results of calculation of a delay time for scanning line A and the principle of transmission.
Figure 28B:
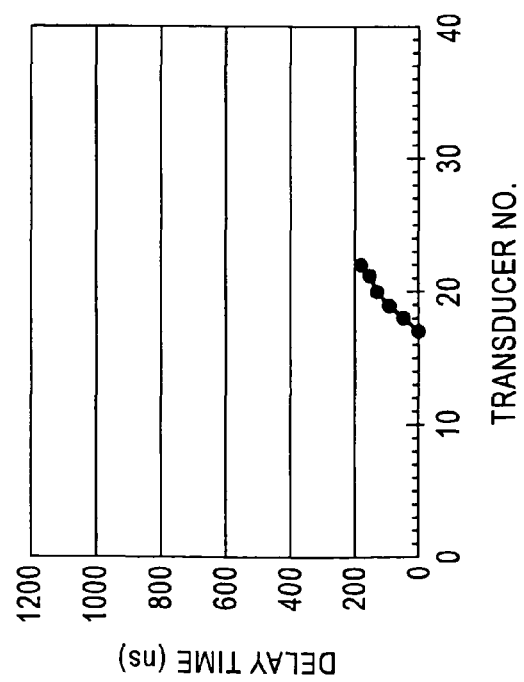

FIG. 28 shows the results of calculating the delay time for scanning line A shown in FIG. 27A and the principle of wave transmission. In the drawing, 10 represents a flaw inspection condition calculating unit configured to calculate 1) to 8) above, 11 represents a delay time setting unit configured to determine transmission timings for transmission pulses on the basis of the flaw inspection conditions, 12 represents a pulser, and 13 represents each transducer in the linear array probe 5. The drawing shows that only the transducers numbered 17 to 22 are selected, the transducer No. 17 is vibrated first, and the transducers Nos. 18 to 22 are sequentially vibrated with time delays. In this manner, a transmission beam corresponding to scanning line A is formed.

Figures 29A, 29B:
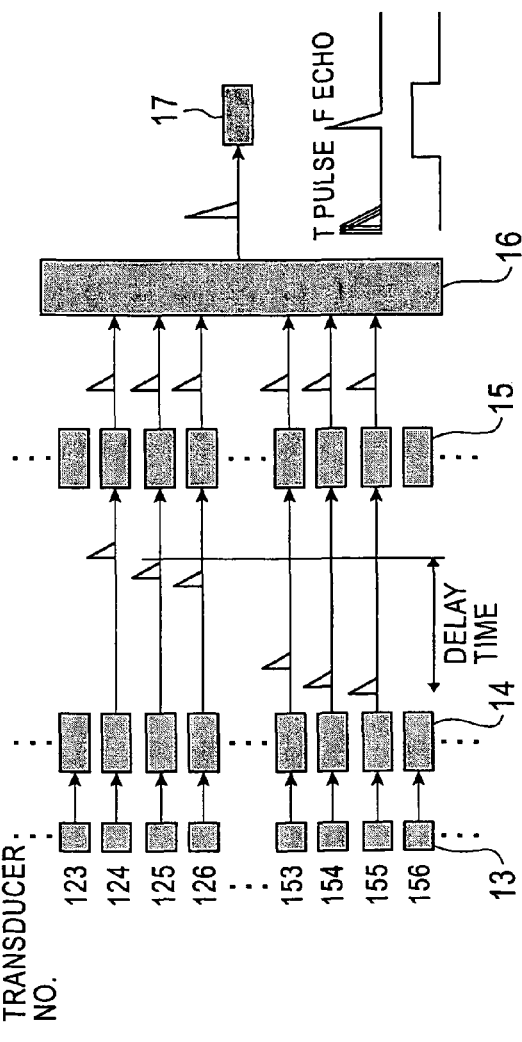
FIGS. 29A and 29B are diagrams showing the results of calculation of a delay time for scanning line C and the principle of reception.

FIGS. 29A and 29B show the results of calculating the delay time for scanning line C shown in FIG. 27A and the principle of wave reception. In the drawing, 13 represents each transducer in the linear array probe, 14 represents a reception amplifier, 15 represents a delay time setting unit, 16 represents an integration processing unit, and 17 represents a gate evaluation unit. The drawing shows that only the transducers numbered 124 to 155 are selected, an echo from the flaw first enters the transducer No. 124 and is sequentially received by the transducers Nos. 125 to 155 with time delays, the time delays are corrected in the delay time setting unit 15 to conduct phase matching, the signals are integrated in the integration processing unit 16, and thus the echo is intensified by a focusing effect.

The wave reception corresponding to scanning line C is conducted by such an operation. Subsequently, in the gate evaluation unit 17, whether a flaw echo (F echo in the drawing) is present in the time range (gate) set to a distance corresponding to the beam path from the transmission pulse (T pulse in the drawing) is evaluated to detect flaws. The processes carried out by the delay time setting unit 15, the integration processing unit 16, and the gate evaluation unit 17 can also be carried out by immediately subjecting signals output from the reception amplifiers 14 to A/D conversion, storing the resultant signals in a memory, and processing the signals using software.

Although calculation of the flaw inspection conditions described above is conducted sequentially after the point of incidence of each scanning line is determined, the order of calculation is not limited to this. For example, the focal position may be determined first, and then the shortest path through which the propagation time to the focal position is the shortest may be determined for each transducer by exploratory analysis.

In tandem flaw inspection, in order to evaluate the mechanical properties of the welded zone of the electric resistance welded steel pipe, the beam width of the ultrasound transmitted or received needs to be 0.5 to 2.5 mm. The focusing coefficient, which is one of the parameters expressing the focusing degree of the beam, also has an applicable range. The focusing coefficient J is the value indicating the increase in sound pressure at the focusing position:

$$J = 20 \log\left(\frac{D^2}{4\lambda F}\right) \quad (2)$$

In the equation, D represents the aperture width of a transducer, F represents the focal length, and λ represents the wavelength. In equation (2), the focal length F and the wavelength λ are values converted into values in water.

Figure 30:
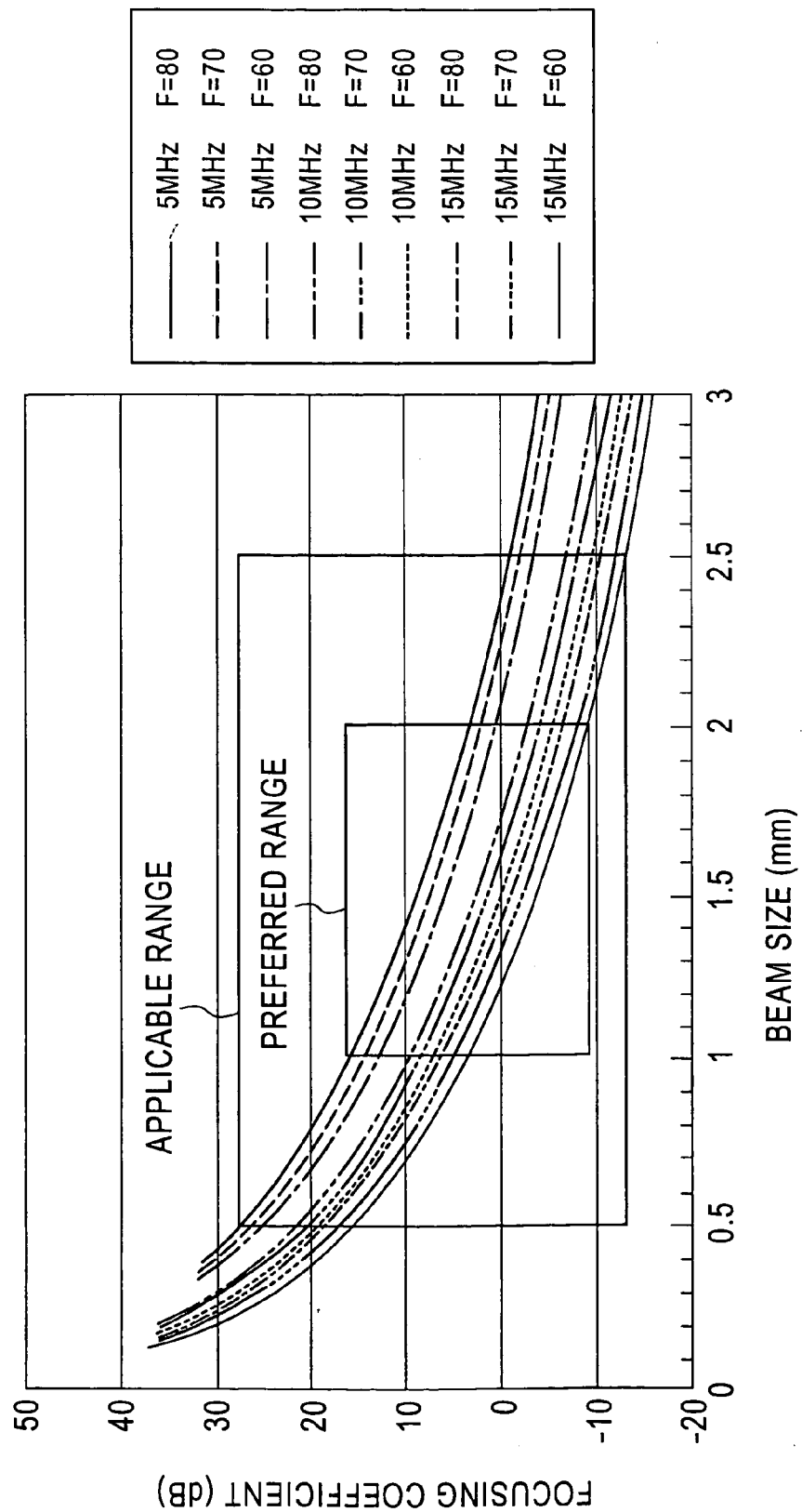
FIG. 30 is a diagram showing the relationship between the focusing coefficient and the beam size.

FIG. 30 shows the results theoretical calculation of the relationship between the focusing coefficient and the beam width (beam width, in FIG. 30, "beam size" is indicated) under conditions of a frequency of 5 MHz to 15 MHz and a focal length F=60 mm to 80 mm (substantially corresponding to the steel pipe thickness range of 10 mm to 16 mm) by using equation (2). As apparent from these results, the smaller the beam width (beam size), the larger the focusing coefficient, and the larger the beam width, the smaller the focusing coefficient. Since the focusing coefficient is the value indicating an increase in sound pressure, a higher value is preferred.

However, in detecting the scattered-type penetrators taking form of minute flaws distributed over a wide region, the beam width becomes below the suitable range if the focusing coefficient is large. Thus, care must be taken to adjust the beam width in the optimum range. For example, the focusing coefficient range corresponding to the ultrasound beam width of about 0.5 to 2.5 mm, i.e., the width applicable for detecting the scattered-type penetrators, is −13 dB to 28 dB, directly. However, considering the beam width, the applicable range of the focusing coefficient is about −5 to 20 dB. For the preferable beam width range of about 1.0 to 2.0 mm, the focusing coefficient is about −10 dB to less than 5 dB, and this is the applicable range of the focusing coefficient.

EXAMPLES

Examples in which the quality control method by tandem flaw inspection shown in the embodiment is applied to a production process for an electric resistance welded steel pipe will now be described.

Figure 31:
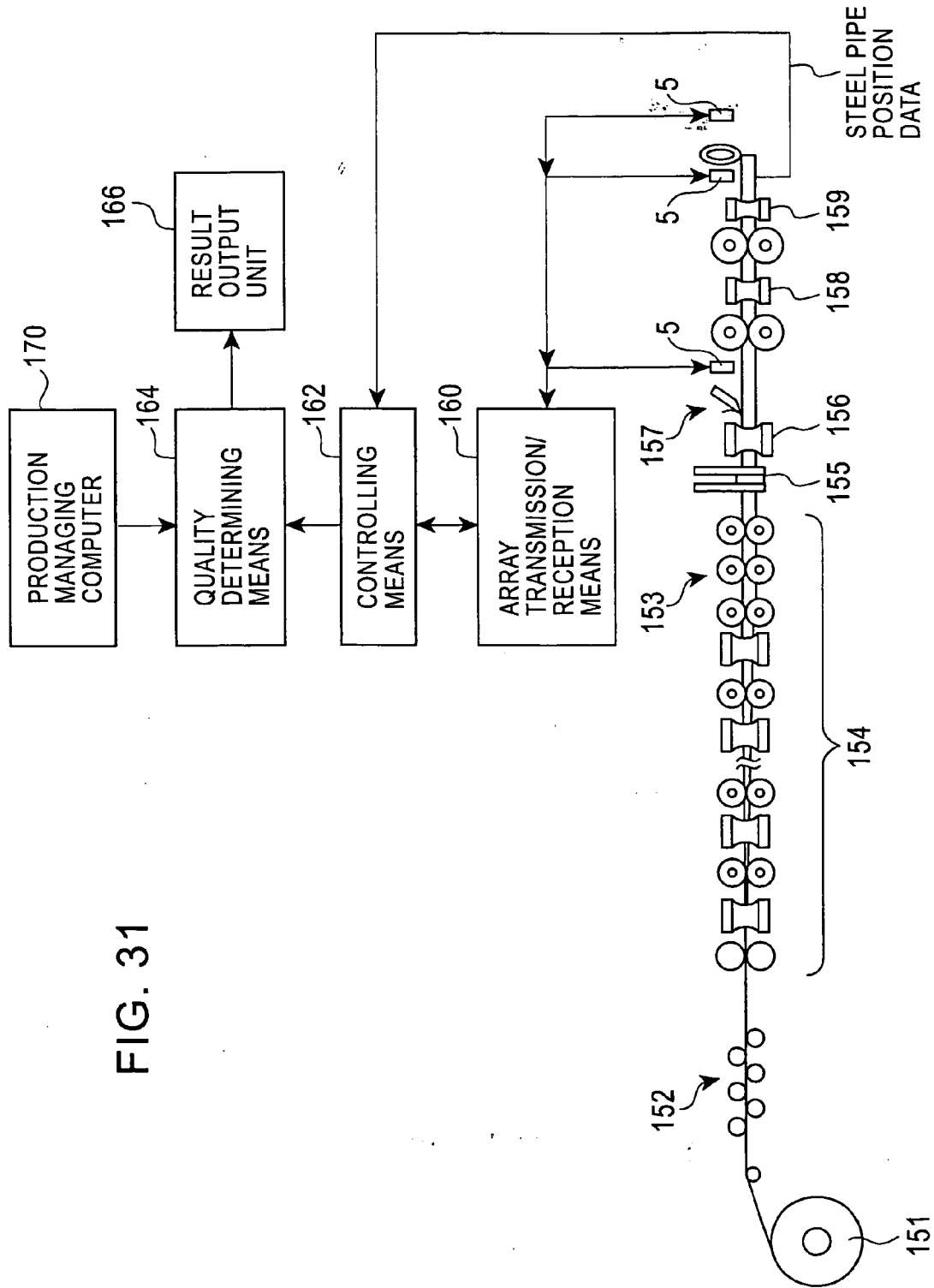
FIG. 31 is a diagram illustrating an example of the present invention.

FIG. 31 is a diagram illustrating an example of a system applied to the electric resistance welded steel pipe production process. The system includes an uncoiler 151 that supplies a strip, and a leveler 152, a roll extruder 154, a fin-pass extruder 155, an induction heater 156, a squeeze roll 157, and a sizer 158 that correct the shape. For example, a strip having a width of 1920 mm and a thickness of 19.1 mm is electroseamed and passed through the sizer 158 to produce a φ600 steel pipe. In the drawing, 159 represents a pipe cutter.

The quality can be controlled by, for example, providing an array probe 5 for tandem flaw inspection at the entry or delivery side of the sizer 158 after completion of welding or at the delivery side of pipe cutter 159 and evaluating the mechanical properties on the basis of the results. The system includes array transmission/reception means 160 configured to conduct transmission and reception by the array probe 5, controlling means 162 configured to control various conditions including the beam width, the aperture width, the angle of incidence on the steel pipe, etc., in transmission and reception with the array probe 5, quality determining means 164 configured to determine presence of flaws in welded zone and the mechanical properties on the basis of signals received by the array probe 5, and a result output unit 166 configured to indicate or print the evaluation results rendered in the quality determining means 164. The correspondences with the function units shown in FIG. 17 are approximately as follows. The array transmission/reception means 160 corresponds to the range including the array transmission unit 36, the array reception unit 37, the array transmission rule memoryunit 34, and the array reception rule memory unit 35. The controlling means 162 corresponds to the range including the aperture width controlling unit 32, the gate position memory unit 33, the gate unit 38, a work size input unit 30, and the array probe memory unit 31. The quality determining means 164 corresponds to the range including the received signal storing unit 56, the signal processing unit 58, the parameter input means 60, the detection threshold input unit 39, and the index value-mechanical properties association data 64.

In storing the received signal data on the received signal storing unit 56 shown in FIG. 17, the data indicating the flaw inspection position in the thickness direction may be input from the controlling means since scanning is conducted by controlling the transducers in the array probe 5, and the flaw inspection position in the pipe axial direction may be input from the sensor that detects the travelling distance of the steel pipe in the production line. As for the conditions such as the size of the steel pipe, a production managing computer 170 may be coupled to the quality determining means 164 (or controlling means 162) so that the data can be input. If other inspection conditions need to be changed depending on the type of the steel pipe, the data may be input from the production managing computer 170 as needed.

Industrial Applicability

According to the present invention, flaws such as penetrators can be adequately determined and detected. Thus, the welding process can be improved to avoid occurrence of minute flaws that affect the mechanical properties of welded zones of welded steel pipes and quality control that can screen the products to prevent flawed products can be achieved. Thus, the quality of the welded steel pipes can be drastically improved and the welded steel pipes can be used in operation conditions more stringent than conventionally practiced.

What is claimed is:

1. A quality control method for a pipe, comprising:
    subjecting a welded zone of a pipe to ultrasonic flaw detection at least in a pipe axial direction,
    detecting scattered-type penetrator flaws within a predetermined area of the welded zone, and
    evaluating a quality of the pipe using observed values relating to the scattered-type penetrator flaws in units of the predetermined area in a pipe thickness direction and the pipe axial direction.

2. The quality control method according to claim 1, wherein a length of one side of the predetermined area is an ultrasound beam width or more and a pipe thickness or less.

3. The quality control method according to claim 1, wherein the quality of the pipe is evaluated while shifting the predetermined area in the pipe axial direction.

4. The quality control method according to claim 1, wherein the quality of the pipe is evaluated while shifting the predetermined area in the pipe thickness direction.

5. The quality control method according to claim 1, wherein the quality of the pipe is evaluated using an average value of the observed values within the predetermined area.

6. The quality control method according to claim 5, wherein among predetermined areas in the pipe thickness direction, a maximum average value at the same position in the pipe axial direction is determined and the quality of the pipe is evaluated using the maximum average value.

7. The quality control method according to claim 5, wherein among predetermined areas in the pipe thickness direction, a maximum average value in a predetermined pipe-thickness-direction range at the same position in the pipe axial direction is determined and the quality of the pipe is evaluated using the maximum average value.

8. The quality control method according to claim 6, wherein the maximum average value at each position in the pipe axial direction is plotted into a chart.

9. The quality control method according to claim 1, wherein the ultrasonic flaw detection is conducted with an ultrasonic flaw detector comprising:
    a transmission unit configured to transmit an ultrasound to a welded surface of a welded zone of the pipe, the welded zone extending in the pipe axial direction, and
    a reception unit configured to receive part or all of a reflected wave from the welded surface,
    wherein the transmission unit and the reception unit comprise transmission/reception units having different transducer groups on one or two or more array probes arranged in a pipe circumferential direction.

10. The quality control method according to claim 9, wherein the transmission unit transmits an ultrasound so that the ultrasound is incident on the welded surface of the welded zone of the pipe, the welded zone extending in the pipe axial direction, and on an inner surface of the pipe respectively at an angle in the range of 33.2° to 56.8°, and
    the reception unit is configured to receive part or all of the reflected wave reflected in a direction within the range of −12° to 16° with respect to a mirror reflection direction at the welded surface.

11. The quality control method according to claim 10, wherein a beam width of the ultrasound is in the range of 0.5 mm to 2.5 mm at the welded surface.

12. The quality control method according to claim 1, wherein a diameter of each scattered-type penetrator flaw of the scattered-type penetrator flaws to be detected is in the order of 10 μm.

13. The quality control method according to claim 1, wherein the scattered-type penetrator flaws to be detected are distributed within the predetermined area.

14. A manufacturing method for a pipe, comprising:
    manufacturing a pipe;
    subjecting a welded zone of the pipe to ultrasonic flaw detection at least in a pipe axial direction;
    detecting scattered-type penetrator flaws within a predetermined area of the welded zone; and
    evaluating a quality of the pipe using observed values relating to the scattered-type penetrator flaws in units of the predetermined area in a pipe thickness direction and the pipe axial direction.

* * * * *